US012724000B2

(12) United States Patent
Ichinari et al.

(10) Patent No.: US 12,724,000 B2
(45) Date of Patent: Sep. 1, 2026

(54) WATER QUALITY METER DATA PROCESSING DEVICE, WATER QUALITY METER DATA PROCESSING SYSTEM AND WATER QUALITY METER DATA PROCESSING METHOD

(71) Applicant: HORIBA Advanced Techno, Co., Ltd., Kyoto (JP)

(72) Inventors: Yuichi Ichinari, Kyoto (JP); Hideki Nakayama, Kyoto (JP); Manabu Shibata, Kyoto (JP); Yasuto Kaba, Kyoto (JP); Daisuke Irikura, Kyoto (JP)

(73) Assignee: HORIBA Advanced Techno, Co., Ltd., Kyoto (JP)

(*) Notice: Subject to any disclaimer, the term of this patent is extended or adjusted under 35 U.S.C. 154(b) by 435 days.

(21) Appl. No.: 18/250,395

(22) PCT Filed: Oct. 26, 2021

(86) PCT No.: PCT/JP2021/039418
§ 371 (c)(1),
(2) Date: Apr. 25, 2023

(87) PCT Pub. No.: WO2022/092058
PCT Pub. Date: May 5, 2022

(65) Prior Publication Data

US 2023/0366848 A1 Nov. 16, 2023

(30) Foreign Application Priority Data

Oct. 28, 2020 (JP) ................................ 2020-180605
Nov. 25, 2020 (JP) ................................ 2020-195463

(51) Int. Cl.
*G01N 27/30* (2006.01)
*G01N 27/327* (2006.01)
*G01N 33/18* (2006.01)

(52) U.S. Cl.
CPC ....... *G01N 27/302* (2013.01); *G01N 27/3274* (2013.01); *G01N 33/18* (2013.01)

(58) Field of Classification Search
CPC ... G01N 27/302; G01N 27/3274; G01N 33/18
See application file for complete search history.

(56) References Cited

U.S. PATENT DOCUMENTS

2012/0223902 A1 9/2012 Ida
2016/0033465 A1* 2/2016 Schreiber ................ G06F 16/22 702/50
2019/0390990 A1* 12/2019 Krywyj ..................... G01L 9/04

FOREIGN PATENT DOCUMENTS

CN 106662564 A 5/2017
JP 2002503331 A 1/2002
(Continued)

OTHER PUBLICATIONS

JP2007/003311, machine translation (Year: 2007).*
(Continued)

*Primary Examiner* — Lam S Nguyen
(74) *Attorney, Agent, or Firm* — Alleman Hall LLP

(57) ABSTRACT

A water quality meter data processing device that processes measurement value data which is data pertaining to measurement values resulting from measurement by a water quality meter of a body being measured, the water quality meter data processing device comprises a measurement value data acquisition unit that acquires the measurement value data, and a memory unit that stores related data which includes data related to at least one of either the body being measured or the water quality meter.

9 Claims, 14 Drawing Sheets

(56) References Cited

FOREIGN PATENT DOCUMENTS

| | | | |
|---|---|---|---|
| JP | 2006300870 | A | 11/2006 |
| JP | 2007003311 | A | 1/2007 |
| JP | 2012098150 | A | 5/2012 |
| JP | 2012184972 | A | 9/2012 |
| JP | 2013142591 | A | 7/2013 |
| JP | 2014202587 | A | 10/2014 |
| JP | 2015510116 | A | 4/2015 |
| JP | 2015172504 | A | 10/2015 |
| JP | 2020139915 | A | 9/2020 |
| WO | 9721090 | A1 | 6/1997 |
| WO | 2013112767 | A1 | 8/2013 |

OTHER PUBLICATIONS

Japan Patent Office, Office Action Issued in Application No. 2022-559142, May 23, 2025, 2 pages.
ISA Japan Patent Office, International Search Report Issued in Application No. PCTJP2021039418, Jan. 25, 2022, WIPO, 8 pages.
Written Opinion of the International Searching Authority issued in Application No. PCTJP2021039418, Jan. 25, 2022, WIPO, 6 pages.
China National Intellectual Property Administration, Office Action Issued in Application No. 202180073284.5, Sep. 26, 2025, 15 pages.
The International Bureau of WIPO, Written Opinion Issued in Application No. PCT/JP2021/039418, May 2, 2023, WIPO, 8 pages.

* cited by examiner (a)
1
Communication unit
1b
1a
Image capture unit
Processing unit
4
Acquisition unit
41
2
Input unit
Output unit
3
21
Touch panel
Memory unit
42
Display
31
22
Button
Arithmetic unit
43
Speaker
32
23
Microphone
Control unit
44
(b)
Processing unit
4
4c
Interface
Memory
4b
Program
4d
4a
Processor

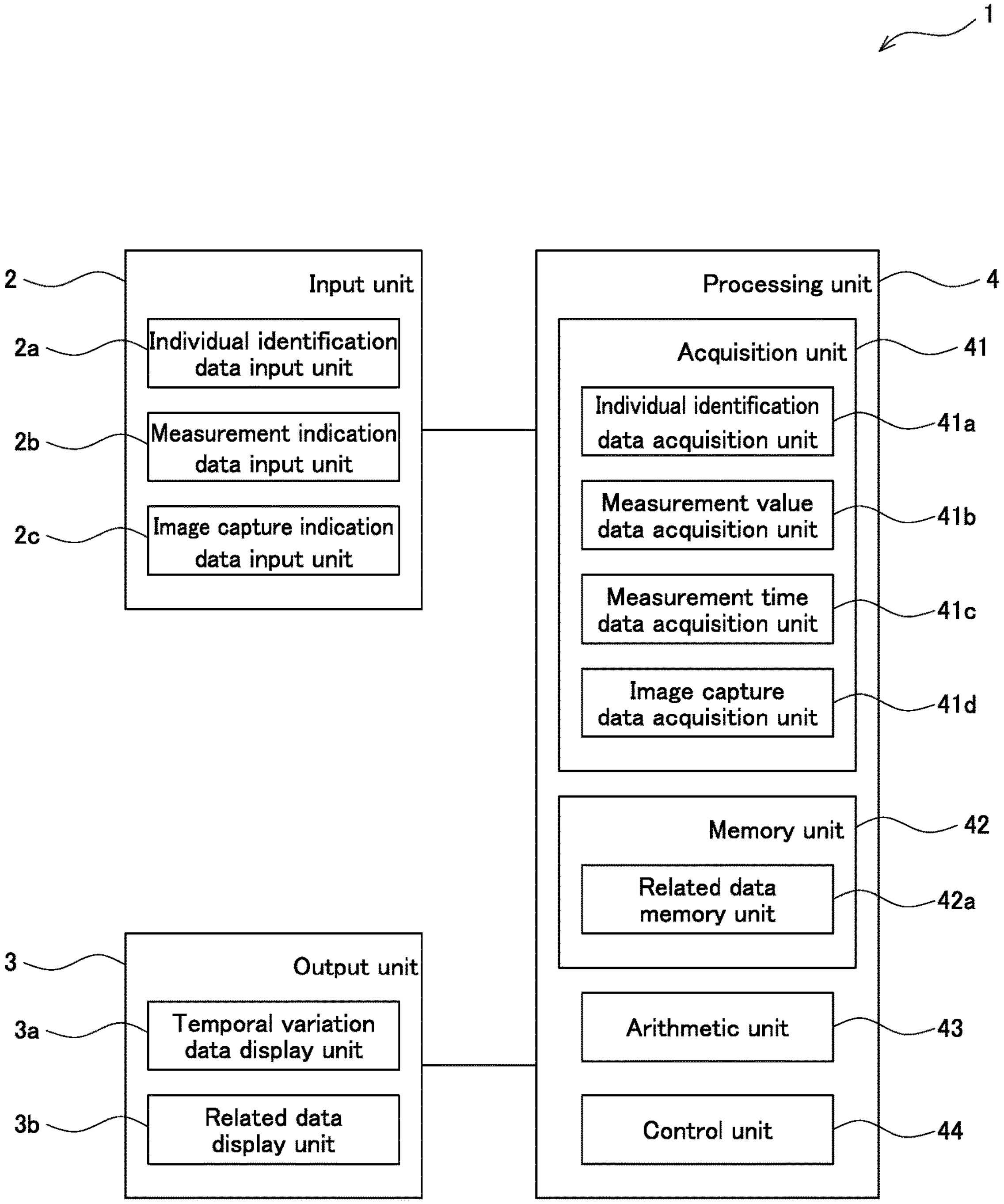

Fig. 3

2 Input unit
2a Individual identification data input unit
2b Measurement indication data input unit
2c Image capture indication data input unit 4 Processing unit
41 Acquisition unit
41a Individual identification data acquisition unit
41b Measurement value data acquisition unit
41c Measurement time data acquisition unit
41d Image capture data acquisition unit
42 Memory unit
42a Related data memory unit
43 Arithmetic unit
44 Control unit 3 Output unit
3a Temporal variation data display unit
3b Related data display unit

| Order | Type | Dispense amount | Tolerance values | | Measurement value | Determination |
|---|---|---|---|---|---|---|
| 1 | Raw Material f | 285mg | Weight | 285±1.4 | 285.9 | ○ |
| 2 | Raw Material g | 325mg | Weight | 325±1.6 | 326.0 | ○ |
| 3 | Pure water | 490ml | pH | 11.0±0.5 | 11.2 | ○ |
| 4 | Raw Material h | 0.58ml | pH | 9.0±0.05 | | |

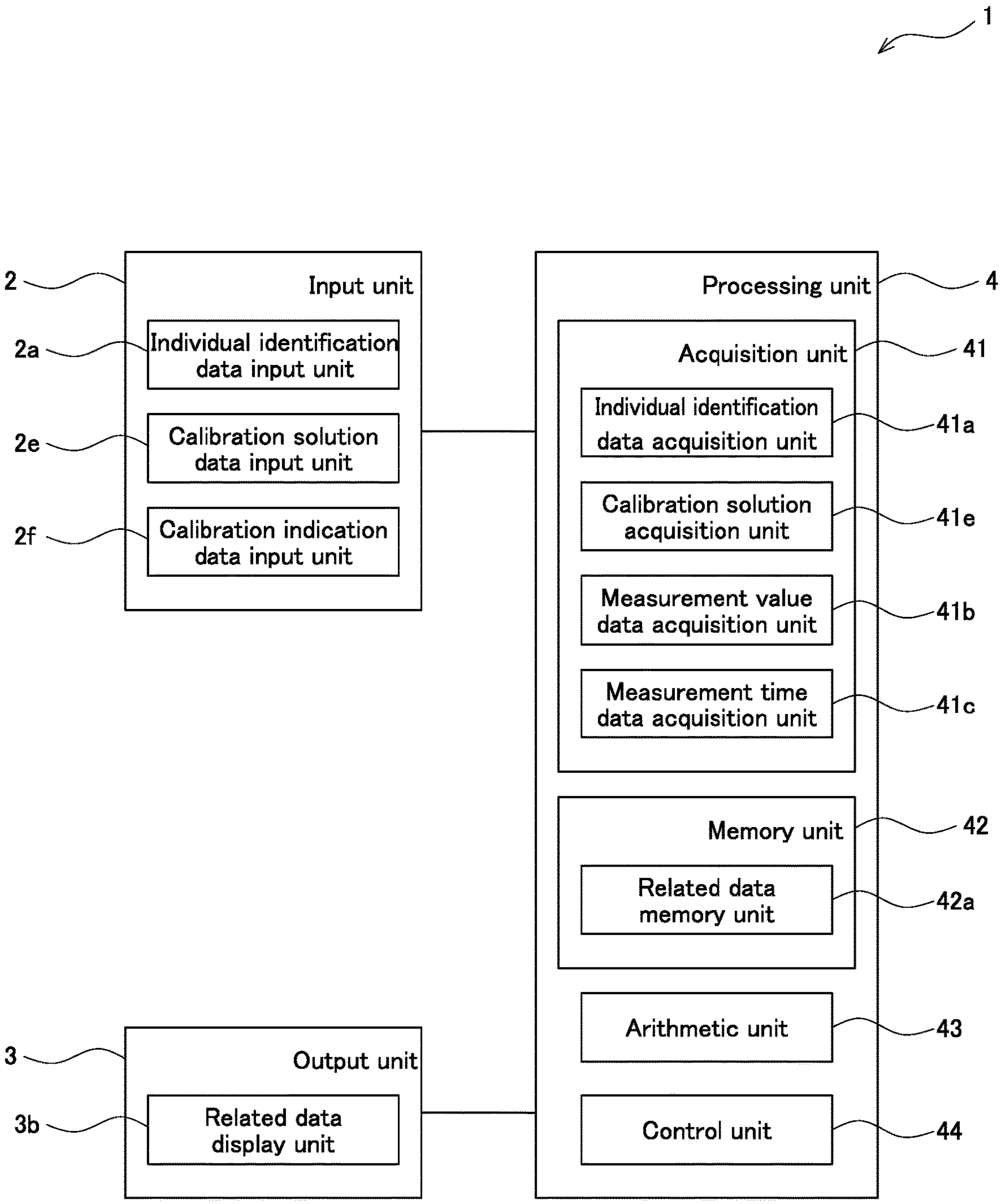

Fig. 11

2 Input unit
2a Individual identification data input unit
2e Calibration solution data input unit
2f Calibration indication data input unit 4 Processing unit
41 Acquisition unit
41a Individual identification data acquisition unit
41e Calibration solution acquisition unit
41b Measurement value data acquisition unit
41c Measurement time data acquisition unit
42 Memory unit
42a Related data memory unit
43 Arithmetic unit
44 Control unit 3 Output unit
3b Related data display unit

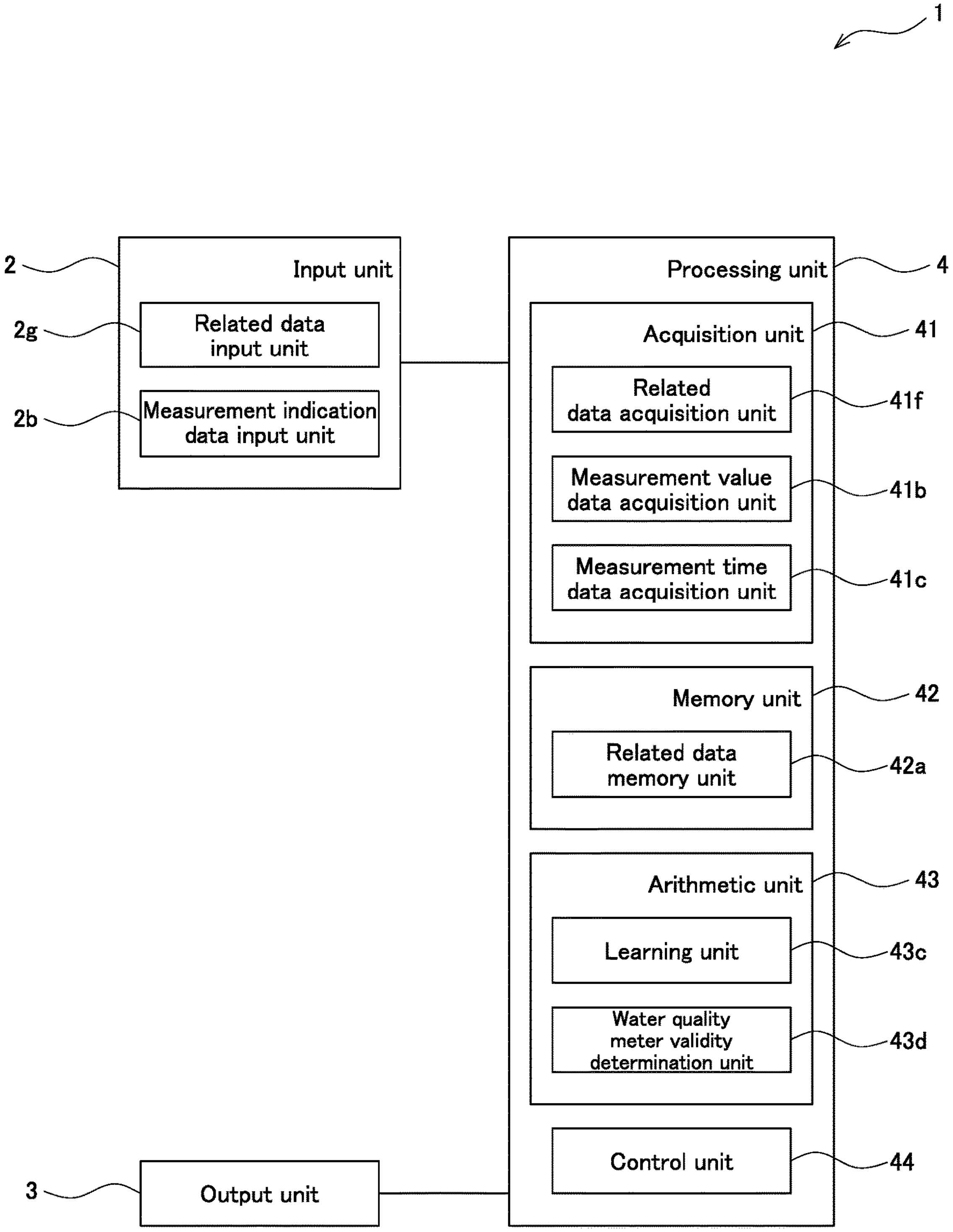

Fig. 13

2 Input unit

2g Related data input unit

2b Measurement indication data input unit

4 Processing unit

41 Acquisition unit

41f Related data acquisition unit

41b Measurement value data acquisition unit

41c Measurement time data acquisition unit

42 Memory unit

42a Related data memory unit

43 Arithmetic unit

43c Learning unit

43d Water quality meter validity determination unit

44 Control unit

3 Output unit

WATER QUALITY METER DATA PROCESSING DEVICE, WATER QUALITY METER DATA PROCESSING SYSTEM AND WATER QUALITY METER DATA PROCESSING METHOD

TECHNICAL FIELD

This application relates to a water quality meter data processing device, a water quality meter data processing system and a water quality meter data processing method.

BACKGROUND ART

Conventionally (e.g., Patent Reference 1) a water quality meter data processing device might, for example, comprise a measurement value data acquisition unit that acquires data (measurement value data) pertaining to measurement values resulting from measurement by a water quality meter (e.g., a pH meter) of a body being measured, and a measurement time data acquisition unit that acquires data (measurement time data) pertaining to measurement times of measurement value data. It so happens that there is a desire that measurement value data be processed in accordance with data related to body or bodies being measured and/or water quality meter(s).

CITATION LIST

Patent Literature

Patent Reference 1: JP 2012-184972 A

SUMMARY OF THE INVENTION

Technical Problem

The problem is therefore to provide a water quality meter data processing device, water quality meter data processing system, and water quality meter data processing method that will allow measurement value data to be processed in accordance with data related to a body or bodies being measured and/or water quality meter(s).

Solution to Problem

There is provided a water quality meter data processing device that processes measurement value data which is data pertaining to measurement values resulting from measurement by a water quality meter of a body being measured, the water quality meter data processing device comprising:

- a measurement value data acquisition unit that acquires the measurement value data; and
- a memory unit that stores related data which includes data related to at least one of either the body being measured or the water quality meter.

Further, the water quality meter data processing device may include a configuration in which:

- the water quality meter data processing device further comprises:
- an individual identification data acquisition unit that acquires individual identification data which is data for individual identification of the body being measured; and
- a measurement time data acquisition unit that acquires measurement time data which is data pertaining to times of measurement by the water quality meter of the body being measured;

- wherein the related data is data relating the individual identification data, the measurement value data, and the measurement time data.

Further, the water quality meter data processing device may include a configuration in which:

- the water quality meter data processing device further comprises:
- an image capture data acquisition unit that acquires image capture data which is data resulting from image capture of the body being measured;
- wherein the related data is data relating the measurement time data and the measurement value data when the body being measured underwent image capture, the image capture data, and the individual identification data.

Further, the water quality meter data processing device may include a configuration in which:

- the related data is reagent preparation data for preparation of a reagent by causing a plurality of raw materials to be dispensed, the related data includes raw material type data which is data pertaining to types of the raw materials, dispense order data which is data pertaining to an order in which the raw materials are dispensed, dispense amount data which is data pertaining to amounts of the raw materials dispensed, and tolerance value data which is data pertaining to tolerance values for the measurement value data when the raw materials are dispensed; and
- the water quality meter data processing device comprises a reagent preparation data display unit that displays the reagent preparation data, and a measurement value data display unit that displays the measurement value data.

Further, the water quality meter data processing device may include a configuration in which:

- the water quality meter is a pH meter that measures a pH of the body being measured;
- the tolerance value data includes tolerance value data for the pH; and
- the measurement value data display unit displays the measurement value data of the body being measured by the pH meter.

Further, the water quality meter data processing device may include a configuration in which:

- the tolerance value data includes tolerance value data pertaining to weights; and
- the measurement value data display unit displays the measurement value data resulting from measurement by a weight gauge of the body being measured.

Further, the water quality meter data processing device may include a configuration in which:

- the water quality meter is a pH meter that causes the measurement value resulting from measurement of the body being measured to be output as an electrical signal;
- the water quality meter data processing device further comprises a calibration solution data acquisition unit that acquires calibration solution data which is data pertaining to a pH of a calibration solution which is the body being measured;
- the measurement value data acquisition unit acquires the measurement value data which is data pertaining to the electrical signal that is output from the pH meter; and
- the related data is data relating the calibration solution data and the measurement value data.

Further, the water quality meter data processing device may include a configuration in which:

the related data is data relating water quality meter validity data which is data pertaining to validity of the water quality meter and measurement value variation data which is data pertaining to variation in the measurement value data as a function of passage of measurement time; and the water quality meter data processing device further comprises:

a learning unit that uses the related data as instructional data to engage in machine learning of a determinative model in which the measurement value variation data serves as input and the water quality meter validity data serves as output; and a water quality meter validity determination unit that uses the determinative model to determine the validity of the water quality meter from a particular one of the measurement value variation data.

Further, there is provided a water quality meter data processing system, which comprises:

at least one water quality meter; and the water quality meter data processing device.

Further, there is provided a water quality meter data processing method that is executed by at least one computer and that is for processing measurement value data which is data pertaining to measurement values resulting from measurement by a water quality meter of a body being measured, the water quality meter data processing method comprising:

acquiring the water measurement value data; and storing related data which includes data related to at least one of either the body being measured or the water quality meter.

BRIEF DESCRIPTION OF THE DRAWINGS

FIG. 3 is a block diagram of control which may occur at a water quality meter data processing device associated with an embodiment.

FIG. 11 is a block diagram of control which may occur at a water quality meter data processing device associated with yet another embodiment.

FIG. 13 is a block diagram of control which may occur at a water quality meter data processing device associated with yet another embodiment.

DESCRIPTION OF EMBODIMENTS

Below, embodiments of a water quality meter data processing system and a water quality meter data processing device are described with reference to FIG. 1 and FIG. 2. At the respective drawings (and the same is true for FIG. 3 through FIG. 14), note that dimensional ratios at the drawings and actual dimensional ratios are not necessarily consistent, and note further that dimensional ratios are not necessarily consistent from drawing to drawing.

Figure 1:
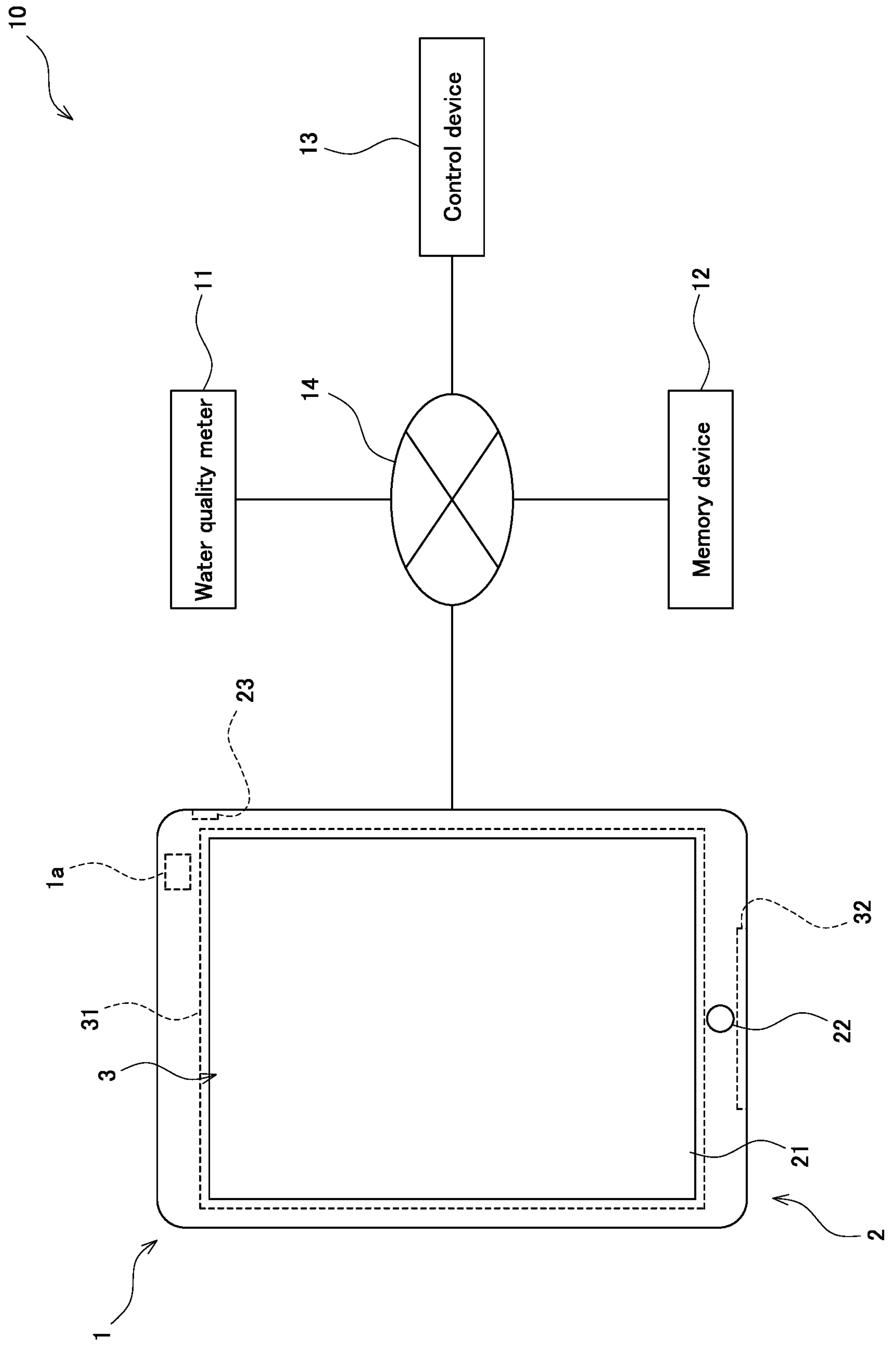
FIG. 1 is a schematic diagram of a water quality meter data processing system.

As shown in FIG. 1, water quality meter data processing system (hereinafter also referred to as simply "processing system") 10 comprises at least one water quality meter 11, and water quality meter data processing device (hereinafter also referred to as simply "processing device") 1 which processes data from measurement by water quality meter 11 of body (see FIG. 4) X1 being measured. Note that processing system 10 may, as is the case in the present embodiment, comprise memory device 12 which stores various types of data, and control device 13 which controls the overall system.

In addition, the respective devices 1, 12, 13 and a plurality of water quality meters 11 are made capable of mutual communication by way of wireless communication means, wired communication means (e.g., wired LAN, communication cables, etc.), and/or other such communication means 14. As wireless communication means, the Internet, Bluetooth, wireless LANs, and the like may be cited as examples. While there is no particular limitation with respect thereto, note that it is also possible, for example, for processing device 1 and water quality meter 11 to be constituted in integral fashion.

So long as it is a measuring instrument that measures a water-related value, there is no particular limitation with regard to water quality meter 11. As water quality meter 11, pH meters, oxidation-reduction potential (ORP) meters, fluorine ion meters, ammonia meters, dissolved oxygen (DO) meters, electrical conductivity meters, resistivity meters, mixed liquor suspended solids (MLSS) meters, turbidimeters, colorimeters, residual chlorine (remaining chlorine) meters, and so forth may be cited as examples.

Processing device 1 might, for example, be a terminal device that is portable and capable of being carried about. Note that processing device 1 may, e.g., as is the case in the present embodiment, be a tablet computer; or it might, for example, be a smart device (smartphone); or it might, for example, be a laptop-type personal computer.

Memory device 12 might, for example, be a server or the like. Furthermore, control device 13 might, for example, be a personal computer or any of various other such computers. Furthermore, the respective owners of water quality meter 11 and respective devices 1, 12, 13 may for example be the same, or they may for example be different.

Processing device 1 comprises input unit 2 at which data is input, and output unit 3 which outputs data. Input unit 2 may, e.g., as is the case in the present embodiment, comprise touch panel 21 at which data is input by causing this to be touched; output unit 3 might, for example, comprise display 31 which displays data. In addition, touch panel 21, which is formed so as to be transparent, might be arranged in layered fashion over the front surface of display 31, that which is displayed at display 31 being visually perceivable by way of touch panel 21.

Input unit 2 may, besides touch panel 21, comprise—as is the case in the present embodiment—button 22 at which data is input by causing this to be pressed upon, and microphone 23 at which data is input in audio fashion. Furthermore, output unit 3 may, as is the case in the present embodiment, comprise speaker 32 at which data is output in audio fashion. Furthermore, processing device 1 may, as is the case in the present embodiment, comprise image capture unit (e.g., sensor(s) having camera functionality) la which captures image(s).

While there is no particular limitation with respect thereto, note that water quality meter 11 and respective devices 12, 13 might for example comprise input units for input of various types of data, and/or might for example comprise acquisition units for acquisition of various types of data, and/or might for example comprise output units for output of various types of data. At processing system 10, input units 2 of respective devices 1 and 11 through 13 are collectively referred to as an input device, and the output units 3 of respective devices 1 and 11 through 13 are collectively referred to as an output device.

Figure 2:
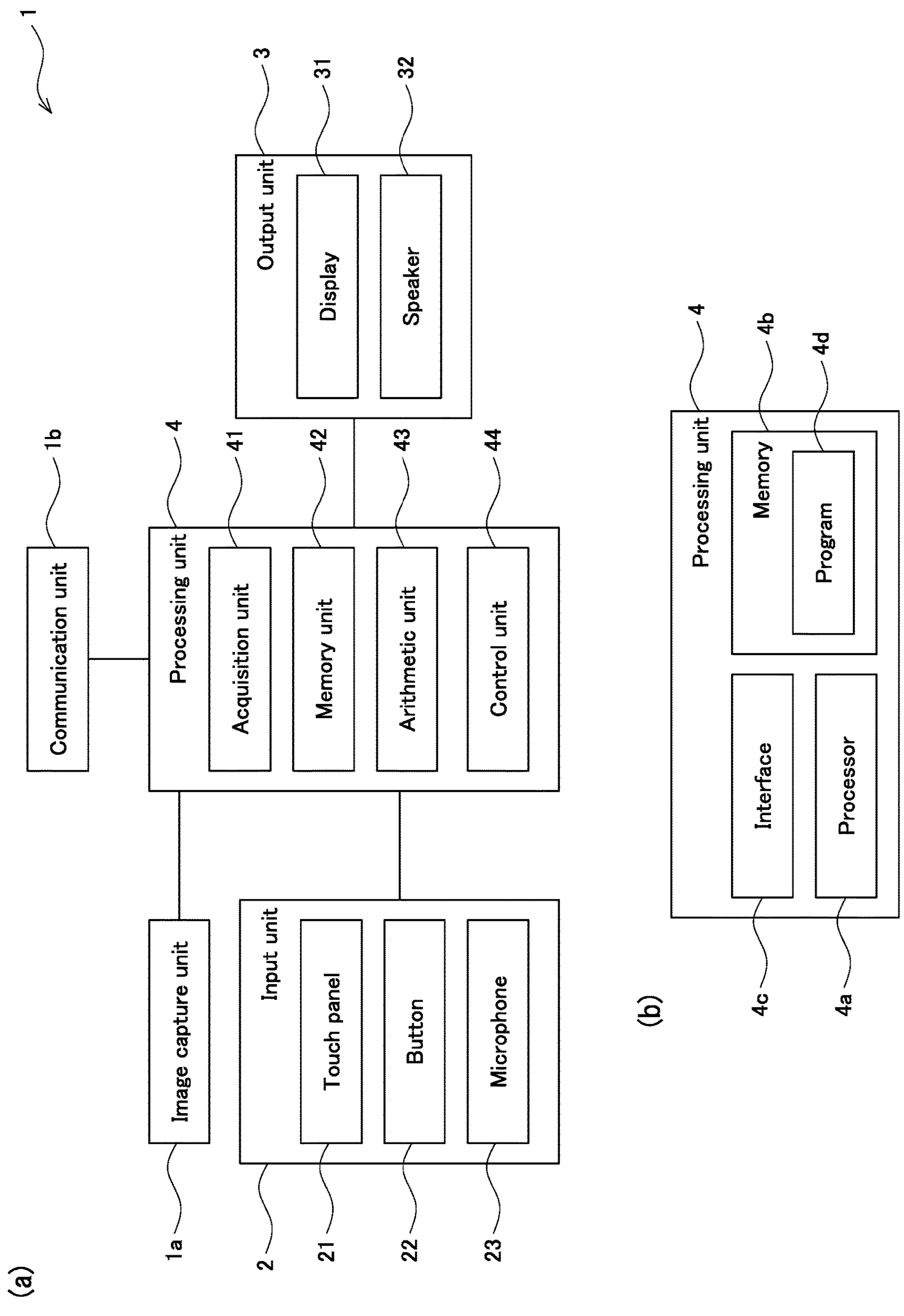
FIG. 2 is a block diagram of control which may occur at a water quality meter data processing device.

As shown at (a) in FIG. 2, processing device 1 comprises processing unit 4 which processes data, and communication unit (e.g., antenna) 1*b* which sends data to and receives data from external units 11 through 13. Processing unit 4 comprises acquisition unit 41 which acquires data, memory unit 42 which stores data, arithmetic unit 43 which performs arithmetic operations with respect to data, and control unit 44 which controls processing device 1 (especially output unit 3) based on data.

Moreover, as shown at (b) in FIG. 2, processing unit 4 is a computer which comprises a CPU, MPU, and/or other such processor(s) 4*a* (e.g., arithmetic unit 43 and control unit 44); ROM, RAM, and/or other such memory or memories 4*b* (e.g., acquisition unit 41 and memory unit 42); various interfaces 4*c* (e.g., acquisition unit 41), and so forth. In addition, program(s) 4*d* stored in memory 4*b* are executed by processor(s) 4*a*, respective units 43, 44 of processing unit 4 being implemented as a result of cooperation between software and hardware.

For example, it is possible to adopt a constitution in which respective units 43, 44 of processing unit 4 are implemented as a result of execution of processing by processor 4*a*, i.e., a single processor 4*a*, at a single computer which is processing device 1. Furthermore, it is possible, for example, to adopt a constitution in which respective units 43, 44 of processing unit 4 are implemented as a result of execution of processing in distributed fashion by processors 4*a*, i.e., a plurality of processors 4*a*, at a plurality of computers such as processing device 1, control device 13, and/or the like.

More specifically, it is possible to adopt a constitution in which at least a portion of control unit(s) 44 and arithmetic unit(s) 43 of processing unit(s) 4 at processing device(s) 1 associated with the first through fourth embodiments, below, are provided at other device(s) (e.g., control device(s) 13 at FIG. 1). Furthermore, while there is no particular limitation with respect thereto, it is possible to adopt a constitution in which, for example, at least a portion of memory unit(s) 42 and acquisition unit(s) 41 of processing unit(s) 4 and output unit(s) 3 and input unit(s) 2 at processing device(s) 1 associated with the first through fourth embodiments, below, are provided at other device(s) (e.g., control device(s) 13 and/or memory device(s) 12 at FIG. 1).

First Embodiment

Below, a first embodiment at a water quality meter data processing device 1 will be described with reference to FIG. 3 through FIG. 5.

As shown in FIG. 3, input unit 2 comprises individual identification data input unit 2*a* at which data (individual identification data) for individual identification of body X1 being measured is input. Furthermore, input unit 2 comprises measurement indication data input unit 2*b* at which data (measurement indication data) for indicating that body X1 being measured is to be measured by water quality meter 11 is input, and image capture indication data input unit 2*c* at which data (image capture indication data) for indicating that image capture is to be carried out by image capture unit 1*a* is input.

Acquisition unit 41 comprises individual identification data acquisition unit 41*a* which acquires individual identification data. Furthermore, acquisition unit 41 comprises measurement value data acquisition unit 41*b* that acquires data (measurement value data) pertaining to measurement values resulting from measurement by water quality meter 11 of body X1 being measured, measurement time data acquisition unit 41*c* that acquires data (measurement time data) pertaining to times of measurement of body X1 being measured by water quality meter 11, and image capture data acquisition unit 41*d* that acquires data (image capture data) resulting from image capture of body X1 being measured.

In addition, when measurement indication data is input at measurement indication data input unit 2*b*, measurement value data acquisition unit 41*b* acquires measurement value data, and measurement time data acquisition unit 41*c* acquires measurement time data. Furthermore, when image capture indication data is input at image capture indication data input unit 2*c*, image capture unit 1*a* carries out image capture, and image capture data acquisition unit 41*d* acquires image capture data.

Memory unit 42 comprises related data memory unit 42*a* which stores related data. In accordance with the present embodiment, related data is data relating measurement time data and measurement value data when body X1 being measured underwent image capture and image capture data and individual identification data. That is, related data includes data (more specifically, individual identification data and image capture data) related to body X1 being measured.

Next, a data processing method for water quality meter data processing device 1 associated with the first embodiment will be described with reference to FIG. 3 through FIG. 5. While there is no particular limitation with respect thereto, note that water quality meter 11 might, e.g., as shown in FIG. 3 through FIG. 5, be a pH meter.

Figure 4:
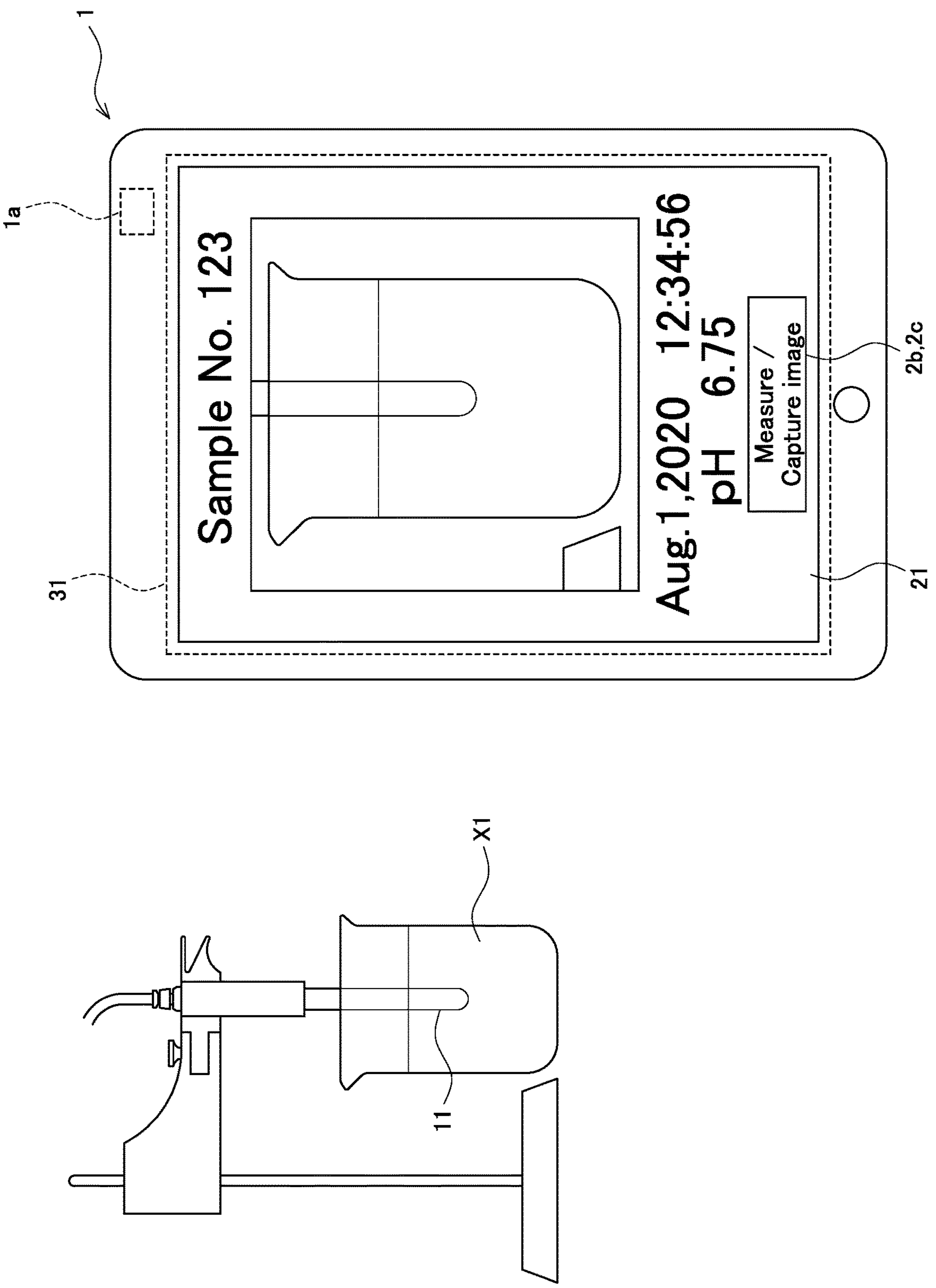
FIG. 4 is a drawing to assist in explaining data processing which may occur at a water quality meter data processing device associated with same embodiment.
Figure 5:
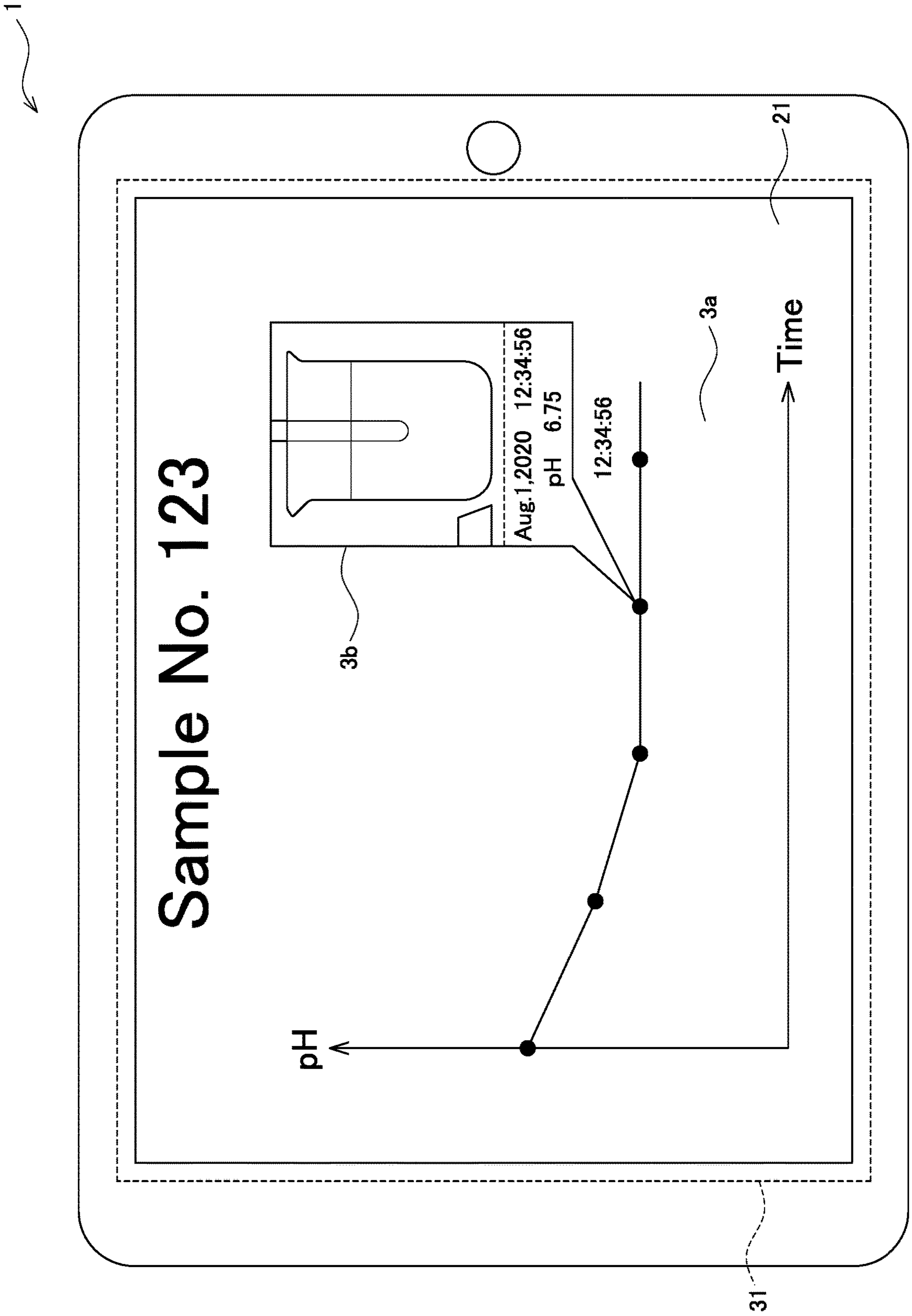
FIG. 5 is a drawing to assist in explaining data processing which may occur at a water quality meter data processing device associated with same embodiment.

For example, where individual identification data has been input at individual identification data input unit 2*a*, and said individual identification data has been acquired by individual identification data acquisition unit 41*a*, this causes said individual identification data to be displayed at display 31 as shown in FIG. 4. At FIG. 4 (and the same is true for FIG. 5), the individual identification data is "Sample No. 123".

Moreover, individual identification data might, for example, be a number and/or the like; and might, for example, be input at individual identification data input unit 2*a* arranged at touch panel 21. Furthermore, individual identification data might, for example, be a bar code, QR code, and/or the like; and might, for example, be input at individual identification data input unit 2*a* by way of image capture unit 1*a* (and/or might be acquired by individual identification data acquisition unit 41*a*).

In addition, if measurement indication data is input at measurement indication data input unit 2*b,* this causes measurement value data acquisition unit 41*b* to acquire measurement value data, and causes measurement time data acquisition unit 41*c* to acquire measurement time data. Furthermore, if image capture indication data is input at image capture indication data input unit 2*c,* this causes image capture unit la to carry out image capture, and causes image capture data acquisition unit 41*d* to acquire image capture data.

Note that it is preferred as shown in FIG. 4 that measurement indication data input unit 2*b* and image capture indication data input unit 2*c* constitute a shared unit, for example. Where this is the case, because it will be possible to make the time at which measurement indication data is input and the time at which image capture indication data is input agree, it will be possible to make the time at which measurement value data is acquired and the time at which image capture data is acquired agree.

In addition, related data, which is data relating measurement time data and measurement value data when body X1 being measured underwent image capture and image capture data and individual identification data, may be stored at related data memory unit 42*a*. At FIG. 4, note that the individual identification data is "Sample No. 123"; the image capture data is an image of body X1 being measured, the measurement value data is "pH 6.75"; and the measurement time data is "Aug. 1, 2020 12:34:56".

In addition, where multiple sets of related data have been stored, arithmetic unit 43 might, for example, perform arithmetic operations with respect to data for the same body X1 being measured based on related data for said body X1 being measured. For example, as shown in FIG. 5, arithmetic unit 43 might perform arithmetic operations with respect to temporal variation data pertaining to measurement values (pH at FIG. 5).

In addition, display 31 may comprise temporal variation data display unit 3*a* which displays temporal variation data pertaining to measurement values, temporal variation data display unit 3*a* displaying said temporal variation data resulting from operations performed by arithmetic unit 43. This will make it possible to confirm temporal variation at said body X1 being measured.

Moreover, display 31 may comprise related data display unit 3*b* which displays respective sets of related data on which said temporal variation data is based. In addition, where, for example, data (related data display indication data) indicating that related data is to be displayed has been input at touch panel 21, related data display unit 3*b* may cause related data to be displayed. In addition, because said related data includes measurement value data, measurement time data, and image capture data, it is also possible, for example, to carry out verification of temporal variation data.

As described above, the water quality meter data processing method, according to this embodiment, that is executed by at least one computer and that is for processing measurement value data which is data pertaining to measurement values resulting from measurement by a water quality meter 11 of a body X1 being measured, the water quality meter data processing method comprises:

acquiring the water measurement value data; and storing related data which includes data related to at least one of either the body X1 being measured or the water quality meter 11 (the body X1 being measured in this embodiment).

Further, the water quality meter data processing system 10 according to this embodiment comprises:

at least one water quality meter 11; and the water quality meter data processing device 1.

Further, the water quality meter data processing device 1, according to this embodiment, that processes measurement value data which is data pertaining to measurement values resulting from measurement by a water quality meter 11 of a body X1 being measured, the water quality meter data processing device 1 comprises:

a measurement value data acquisition unit 41*b* that acquires the measurement value data; and a memory unit 42 that stores related data which includes data related to at least one of either the body X1 being measured or the water quality meter 11 (the body X1 being measured in this embodiment).

In accordance with such constitution, measurement value data, which is data pertaining to measurement values resulting from measurement by water quality meter 11 of body X1 being measured, is acquired; and related data, which includes data related to at least one of either body X1 being measured or water quality meter 11, is stored. This will make it possible for processing of measurement value data to be carried out in accordance with data related to water quality meter 11 and/or body X1 being measured.

Further, as in this embodiment, it may be that the water quality meter data processing device 1 further comprises:

an individual identification data acquisition unit 41*a* that acquires individual identification data which is data for individual identification of the body X1 being measured; and a measurement time data acquisition unit 41*c* that acquires measurement time data which is data pertaining to times of measurement by the water quality meter 11 of the body X1 being measured;

wherein the related data is data relating the individual identification data, the measurement value data, and the measurement time data.

In accordance with such constitution, individual identification data, which is data for individual identification of body X1 being measured, is acquired; and measurement time data, which is data pertaining to times at which body X1 being measured was measured by water quality meter 11, is acquired. In addition, because related data is data relating measurement time data and measurement value data and individual identification data, this will make it possible to confirm temporal variation at body X1 being measured.

Further, as in this embodiment, it may be that the water quality meter data processing device 1 further comprises:

an image capture data acquisition unit 41*d* that acquires image capture data which is data resulting from image capture of the body X1 being measured;

wherein the related data is data relating the measurement time data and the measurement value data when the body X1 being measured underwent image capture, the image capture data, and the individual identification data.

In accordance with such constitution, image capture data resulting from image capture of body X1 being measured is acquired. In addition, because related data is data relating the aforesaid measurement time data and measurement value data when body X1 being measured underwent image capture and image capture data and individual identification data, it is possible to confirm temporal variation at body X1 being measured, and it is moreover possible to cause evidence that it is data pertaining to said body X1 being measured to remain.

Note that processing system 10, processing device 1, and the processing method are not limited to the constitution and action of processing system 10, processing device 1, and the processing method associated with the foregoing first embodiment. For example, modifications such as the following may be made to processing system 10, processing device 1, and the processing method associated with the foregoing first embodiment.

(1) The constitution of processing device 1 associated with the foregoing first embodiment is such that it comprises image capture data acquisition unit 41*d* which acquires image capture data, and related data is data which includes image capture data. However, processing device 1 is not limited to such constitution. For example, it is also possible to adopt a constitution at processing device 1 in which related data does not include image capture data but is data relating only measurement time data and measurement value data and individual identification data.

(2) Furthermore, it is also for example possible to adopt a constitution at processing device 1 associated with the foregoing first embodiment in which, when image capture unit la is capturing an image, acquisition unit 41 acquires audio data which is input at microphone 23, and memory unit 42 stores said audio data. In addition, it is also possible to adopt a constitution in which said audio data that has been stored is related to measurement time data and measurement value data when body X1 being measured underwent image capture and image capture data and individual identification data, and is stored in the form of related data by related data memory unit 42*a*.

Second Embodiment

Next, a second embodiment at a water quality meter data processing device 1 will be described with reference to FIG. 6 and FIG. 7. At FIG. 6 and FIG. 7, note that portions assigned reference numerals identical to reference numerals at FIG. 1 through FIG. 5 indicate elements having constitutions more or less similar to, or functions (actions) more or less similar to, those described above, and that repetitive description thereof is omitted.

Figure 6:
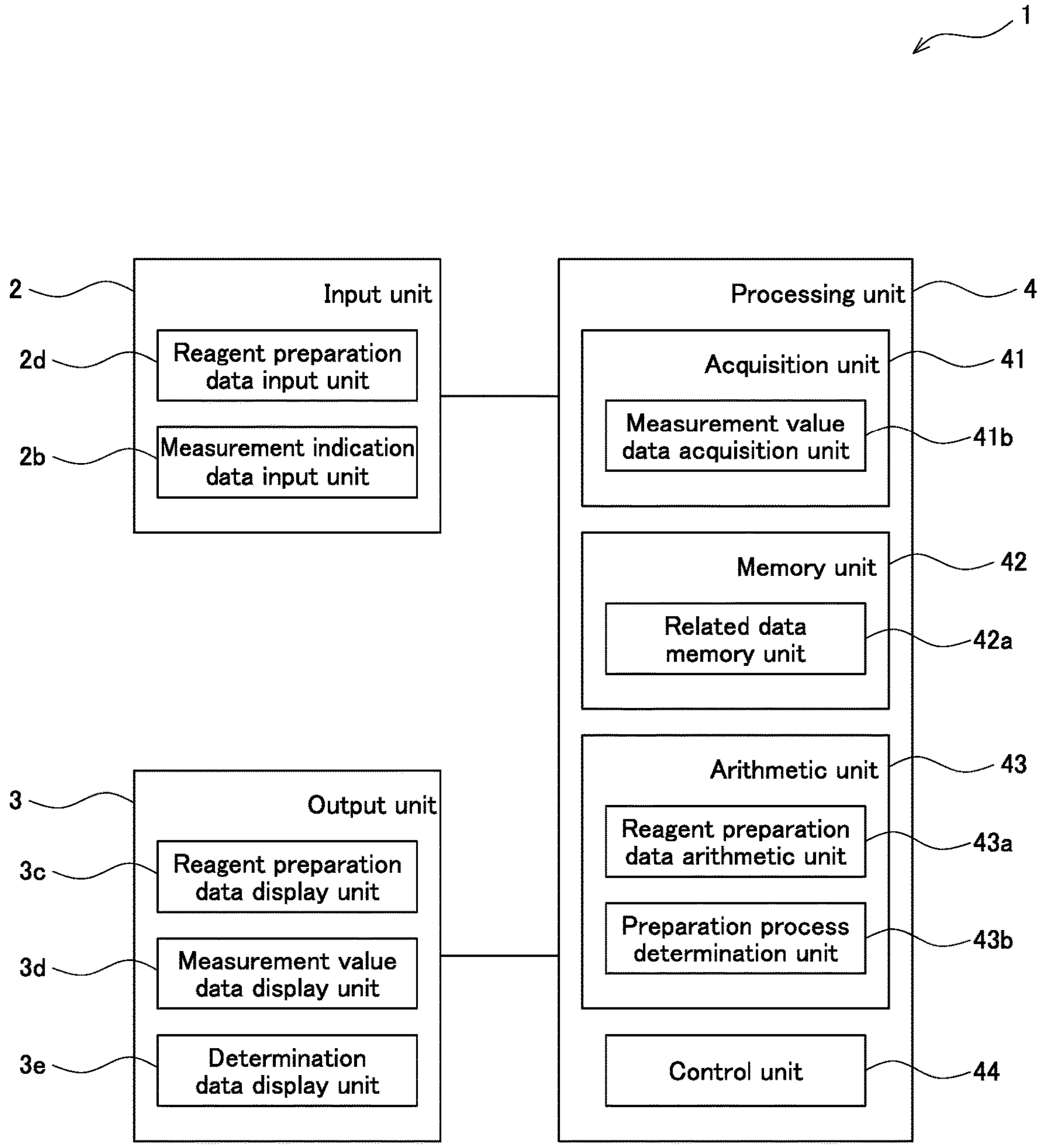
FIG. 6 is a block diagram of control which may occur at a water quality meter data processing device associated with another embodiment.
Figure 7:
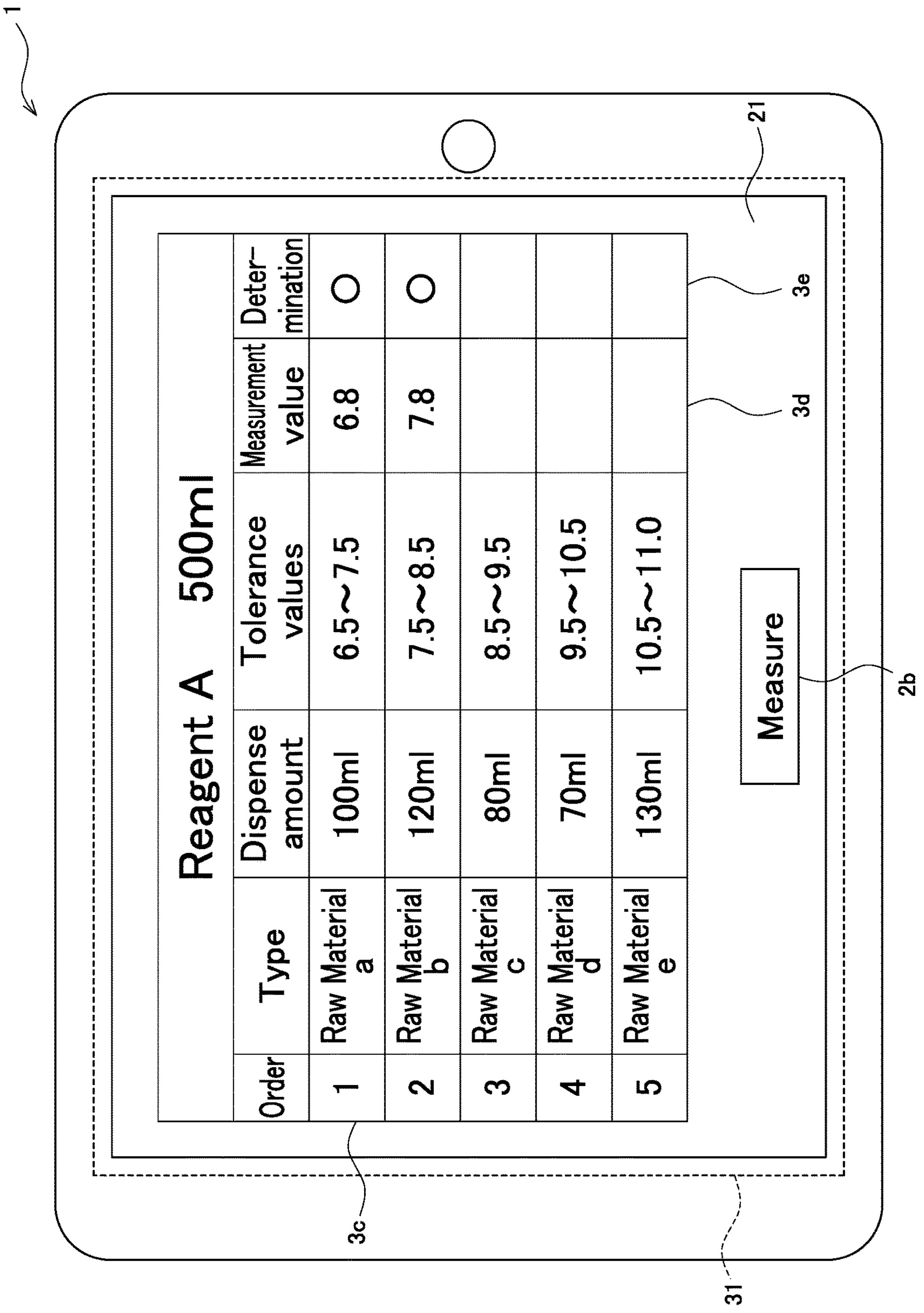
FIG. 7 is a drawing to assist in explaining data processing which may occur at a water quality meter data processing device associated with same embodiment.

As shown in FIG. 6 and FIG. 7, input unit 2 comprises reagent preparation data input unit 2*d* at which reagent preparation data for preparation of a reagent by causing a plurality of raw materials to be dispensed is input. Furthermore, input unit 2 comprises measurement indication data input unit 2*b* at which data (measurement indication data) for indicating that body X1 being measured is to be measured by water quality meter 11 is input.

Note that reagent preparation data includes data pertaining to types of raw materials (raw material type data), data pertaining to order in which raw materials are dispensed (dispense order data), data pertaining to amounts of raw materials dispensed (dispense amount data), and data pertaining to tolerance values for measurement value data when raw materials are dispensed (tolerance value data). Furthermore, reagent preparation data includes data pertaining to the type of reagent being prepared (preparation type data) and data pertaining to the amount of the reagent being prepared (preparation amount data).

Acquisition unit 41 comprises measurement value data acquisition unit 41*b* which acquires data (measurement value data) pertaining to measurement values resulting from measurement by water quality meter 11 of body X1 being measured. In addition, when measurement indication data is input at measurement indication data input unit 2*b,* measurement value data acquisition unit 41*b* acquires measurement value data.

Memory unit 42 comprises related data memory unit 42*a* at which related data is stored. In accordance with the present embodiment, related data is reagent preparation data. That is, related data includes data (more specifically, respective sets of data pertaining to reagent preparation data) related to body X1 being measured.

Arithmetic unit 43 comprises reagent preparation data arithmetic unit 43*a* which performs arithmetic operations with respect to reagent preparation data based on related data stored at related data memory unit 42*a*. Furthermore, arithmetic unit 43 comprises preparation process determination unit 43*b* which determines the validity of a reagent preparation process based on measurement value data and tolerance value data.

Output unit 3 comprises reagent preparation data display unit 3*c* which displays reagent preparation data. Furthermore, output unit 3 comprises measurement value data display unit 3*d* which displays measurement value data, and determination data display unit 3*e* which displays data (determination data) pertaining to determinations made by preparation process determination unit 43*b*.

Next, a data processing method for water quality meter data processing device 1 associated with the second embodiment will be described with reference to FIG. 6 and FIG. 7. While there is no particular limitation with respect thereto, note that water quality meter 11 might, e.g., as shown in FIG. 7, be a pH meter.

For example, where preparation type data and preparation amount data have been input at reagent preparation data input unit 2*d,* this will make it possible for reagent preparation data arithmetic unit 43*a* to perform arithmetic operations with respect to reagent preparation data based on related data stored at related data memory unit 42*a,* and for reagent preparation data display unit 3*c* to display reagent preparation data with respect to which arithmetic operations have been performed. More specifically, arithmetic operations are performed, and display is carried out, with respect to dispense order data, raw material type data, dispense amount data, and tolerance value data.

At FIG. 7, the first row from the top is preparation type data and preparation amount data, the first column from the left is dispense order data, the second column from the left is raw material type data, the third column from the left is dispense amount data, and the fourth column from the left is tolerance value data. This will make it possible to prepare 500 ml of Reagent A by dispensing Raw Material a, Raw Material b, Raw Material c, Raw Material d, and Raw Material e in this order in the predetermined amounts.

The tolerance values are tolerance values for the pH of body X1 being measured at the time that the raw materials are dispensed. At FIG. 7, for example, the tolerance values for the pH of body X1 being measured when 100 ml of the first which is Raw Material a is dispensed are 6.5 to 7.5; the tolerance values for the pH of body X1 being measured when 120 ml of the second which is Raw Material b is dispensed are 7.5 to 8.5.

It may happen where pH is outside of the tolerance values therefor that a dispensed raw material, dispensed amount, or the like is mistaken. As each of Raw Material a through Raw Material e is dispensed, it is therefore the case that measurement indication data is input at measurement indication data input unit 2*b*, and measurement value data is acquired by measurement value data acquisition unit 41*b*.

In addition, preparation process determination unit 43*b* determines the validity of the reagent preparation process based on the acquired measurement value data and tolerance value data. More specifically, preparation process determination unit 43*b* determines that this is valid when measurement value data is within tolerance value data, and preparation process determination unit 43*b* determines that this is invalid when measurement value data is outside of tolerance value data.

In addition, measurement value data display unit 3*d* displays the acquired measurement value data, and determination data display unit 3*e* displays determination data resulting from the determination. Because this makes it possible to compare tolerance value data and measurement value data, it is possible to prepare appropriate reagents. At FIG. 7, the fifth column from the left is measurement value data, and the sixth column from the left is determination data.

When preparation process determination unit 43*b* determines that this is invalid, note that output unit 3 may produce output to the effect that this is invalid. For example, speaker 32 may produce audio output; and/or determination data display unit 3*e* might, for example, cause determination data to be displayed in flashing fashion, and/or the entire display 31 might be made to produce a display to the effect that this is invalid.

As described above, the water quality meter data processing device 1, according to this embodiment, that processes measurement value data which is data pertaining to measurement values resulting from measurement by a water quality meter 11 of a body X1 being measured, the water quality meter data processing device 1 comprises:

- a measurement value data acquisition unit 41*b* that acquires the measurement value data; and
- a memory unit 42 that stores related data which includes data related to at least one of either the body X1 being measured or the water quality meter 11 (the body X1 being measured in this embodiment).

In accordance with such constitution, measurement value data, which is data pertaining to measurement values resulting from measurement by water quality meter 11 of body X1 being measured, is acquired; and related data, which includes data related to at least one of either body X1 being measured or water quality meter 11, is stored. This will make it possible for processing of measurement value data to be carried out in accordance with data related to water quality meter 11 and/or body X1 being measured.

Further, as in this embodiment, it may be that the water quality meter data processing device 1 includes a configuration in which:

- the related data is reagent preparation data for preparation of a reagent by causing a plurality of raw materials to be dispensed, the related data includes raw material type data which is data pertaining to types of the raw materials, dispense order data which is data pertaining to an order in which the raw materials are dispensed, dispense amount data which is data pertaining to amounts of the raw materials dispensed, and tolerance value data which is data pertaining to tolerance values for the measurement value data when the raw materials are dispensed; and
- the water quality meter data processing device 1 comprises a reagent preparation data display unit 3*c* that displays the reagent preparation data, and a measurement value data display unit 3*d* that displays the measurement value data.

In accordance with such constitution, related data is reagent preparation data for preparation of a reagent by causing a plurality of raw materials to be dispensed, and includes tolerance value data which is data pertaining to tolerance values for measurement value data when raw materials are dispensed. In addition, because reagent preparation data is displayed, the reagent can easily be prepared. Furthermore, because tolerance value data is displayed and measurement value data is displayed, it is possible to compare tolerance value data and measurement value data. This makes it possible to prepare an appropriate reagent.

Further, as in this embodiment, it may be that the water quality meter data processing device 1 includes a configuration in which:

- the water quality meter 11 is a pH meter that measures a pH of the body X1 being measured;
- the tolerance value data includes tolerance value data for the pH; and
- the measurement value data display unit 3*d* displays the measurement value data of the body X1 being measured by the pH meter.

In accordance with such constitution, tolerance value data includes data pertaining to pH tolerance values, and measurement value data display unit 3*d* displays measurement value data resulting from measurement by a pH meter of body X1 being measured. This makes it possible for pH values of body X1 being measured which are measured by a pH meter and which are displayed by measurement value data display unit 3*d* to be compared with tolerance values which are displayed by reagent preparation data display unit 3*c*.

Note that processing system 10, processing device 1, and the processing method are not limited to the constitution and action of processing system 10, processing device 1, and the processing method associated with the foregoing second embodiment. For example, modifications such as the following may be made to processing system 10, processing device 1, and the processing method associated with the foregoing second embodiment.

(1) Processing device 1 associated with the foregoing second embodiment may be modified so that measurement value data display unit 3*d* displays not only measurement value data resulting from measurement by water quality meter 11 of body X1 being measured but also measurement value data resulting from measurement by other measuring instrument(s) of body X1 being measured. While there is no particular limitation with respect thereto, weight gauge 15 may be employed as other measuring instrument as shown in FIG. 8.

Figure 8:
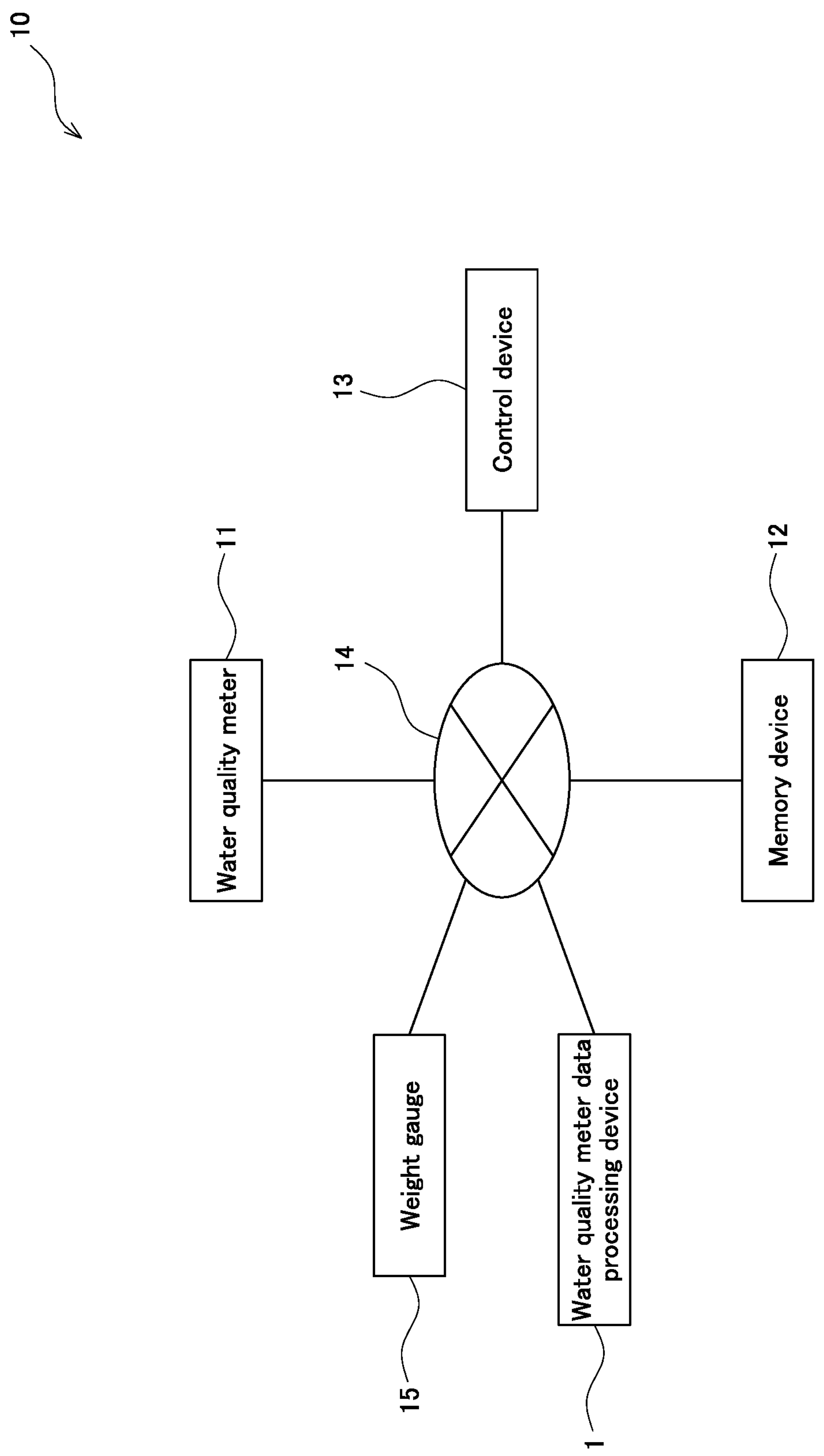
FIG. 8 is a schematic diagram of a water quality meter data processing system associated with a variation on same embodiment.
Figure 9:
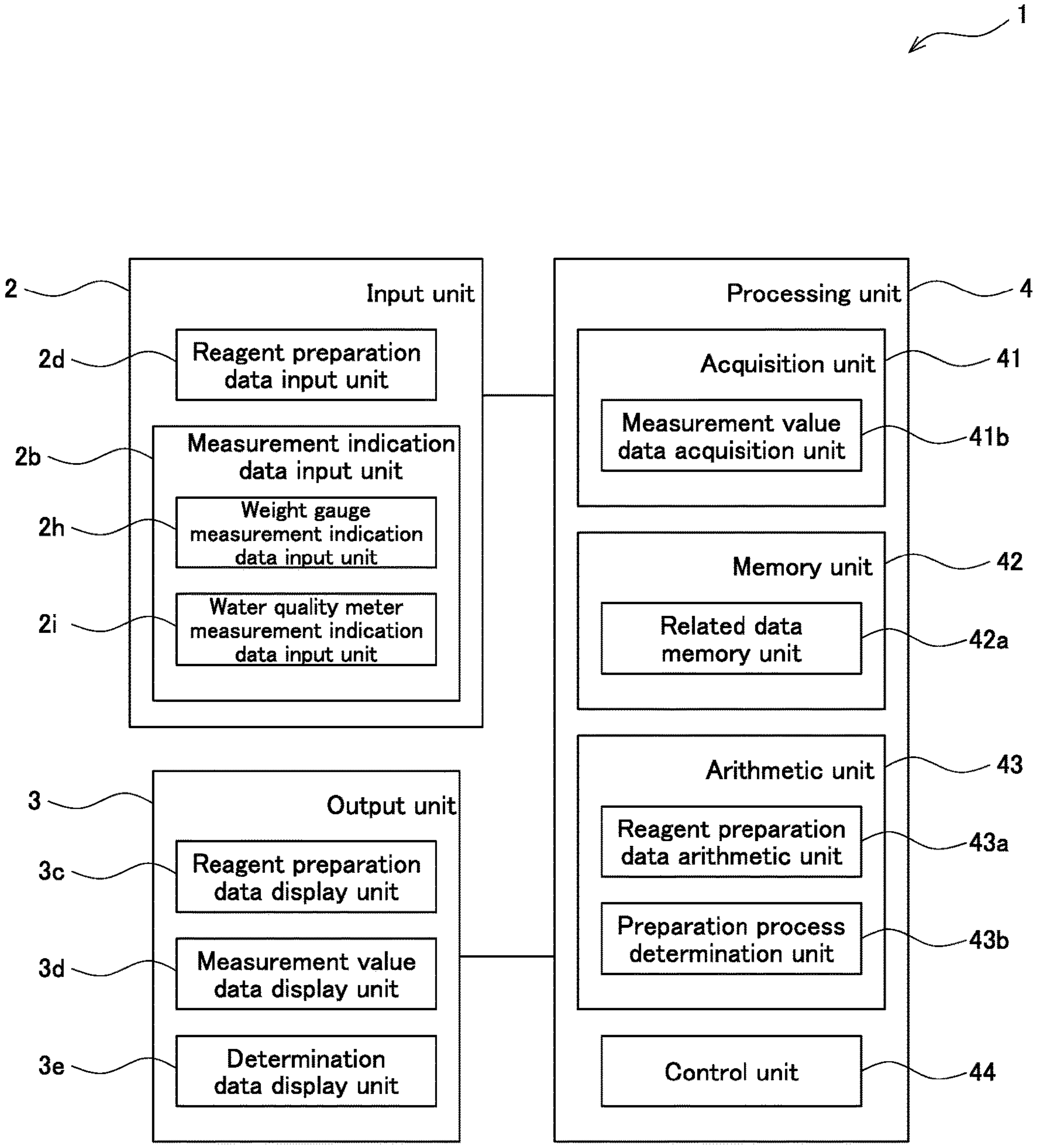
FIG. 9 is a block diagram of control which may occur at a water quality meter data processing device associated with same variation.
Figure 10:
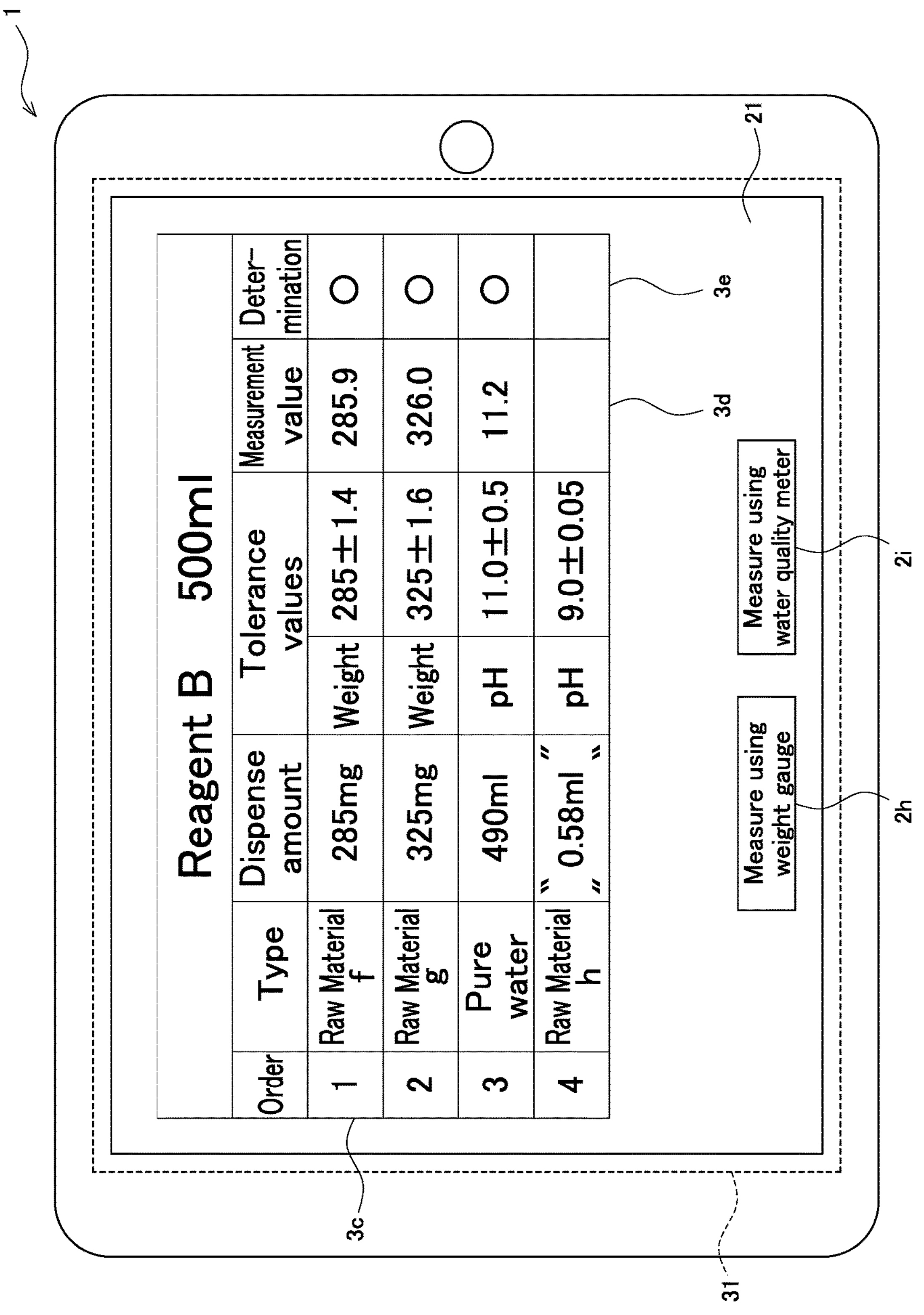
FIG. 10 is a drawing to assist in explaining data processing which may occur at a water quality meter data processing device associated with same variation.

The constitution of processing device 1 associated with FIG. 8 through FIG. 10 is described below.

As shown in FIG. 8 through FIG. 10, input unit 2 might, for example, comprise measurement indication data input unit 2*b* at which data (measurement indication data) for indicating that body X1 being measured is to be measured by measuring instruments 11, 15 is input. For example, measurement indication data input unit 2*b* might comprise weight gauge measurement indication data input unit 2*g* at which measurement indication data for weight gauge (e.g., scale or balance) 15 is input, and water quality meter measurement indication data input unit 2*h* at which measurement indication data for water quality meter (pH meter at FIG. 9 and FIG. 10) 11 is input.

Measurement value data acquisition unit 41*b* might, for example, acquire measurement value data resulting from measurement by water quality meter 11 and weight gauge 15 of body X1 being measured. More specifically, when measurement indication data is input at weight gauge measurement indication data input unit 2*h*, measurement value data acquisition unit 41*b* might acquire measurement value data from weight gauge 15; when measurement indication data is input at water quality meter measurement indication data input unit 2*i*, measurement value data acquisition unit 41*b* might acquire measurement value data from water quality meter 11.

Next, an example of a data processing method for water quality meter data processing device 1 associated with FIG. 8 through FIG. 10 will be described with reference to FIG. 9 and FIG. 10.

For example, where preparation type data and preparation amount data have been input at reagent preparation data input unit 2*d*, this will make it possible for arithmetic operations to be performed, and display to be carried out, with respect to dispense order data, raw material type data, dispense amount data, and tolerance value data as shown in FIG. 10. In addition, this will make it possible to prepare 500 ml of Reagent B by dispensing Raw Material f, Raw Material g, pure water, and Raw Material h in this order in the predetermined amounts.

Moreover, while there is no particular limitation with respect thereto, Raw Material f and Raw Material g are solids (e.g., powders); pure water and Raw Material h are liquids. Accordingly, tolerance values when dispensing Raw Material f and Raw Material g are weight tolerance values; tolerance values when dispensing pure water and Raw Material h are pH tolerance values.

While there is no particular limitation with respect thereto, as Reagent B, tris buffer solution, glycine buffer solution, tricine buffer solution, HEPES buffer solution, phosphate buffer solution, MOPS buffer solution, MES buffer solution, acetate buffer solution, carbonate buffer solution, citrate buffer solution, sodium borate buffer solution, Good's buffer, pentobarbital buffer solution, Clark-Lubs solution (pH 1.0-2.2), p-toluenesulfonate-sodium—p-toluenesulfonate buffer solution, Clark-Lubs solution (pH 2.2-4.0), succinate—NaOH buffer solution, Clark-Lubs solution (pH 4.1-5.9), sodium cacodylate—HCl buffer solution, sodium hydrogen maleate—NaOH buffer solution, Clark-Lubs solution (pH 5.8-8.0), imidazole—HCL buffer solution, 2,4,6-collidine—HCL buffer solution, citrate—Na2HPO4 buffer solution, 2-amino-2-methyl-1,3-propanediol—HCl buffer solution, diethanolamine—HCl buffer solution, sodium carbonate—sodium hydrogen carbonate buffer solution, carbonate buffer solution, phosphate buffer solution, NaoH—KCl buffer solution, β-β'-dimethylglutarate—NaOH buffer solution, and so forth may be cited as examples.

In addition, as each of Raw Material f and Raw Material g is dispensed, measurement indication data is input at weight meter measurement indication data input unit 2*h*, and measurement value data is acquired by measurement value data acquisition unit 41*b* from weight gauge 15. Furthermore, as each of pure water and Raw Material h is dispensed, measurement indication data is input at water quality meter measurement indication data input unit 2*i*, and measurement value data is acquired by measurement value data acquisition unit 41*b* from weight gauge 15.

In addition, preparation process determination unit 43*b* determines the validity of the reagent preparation process based on the acquired measurement value data and tolerance value data, measurement value data display unit 3*d* displays the acquired measurement value data, and determination data display unit 3*e* displays determination data resulting from the determination. While there is no particular limitation with respect thereto, note that data relating respective sets of measurement value data might, for example, be stored by memory unit 42; and moreover, data relating individual information (e.g., reagent numbers) of reagents that have been prepared and respective sets of measurement value data might, for example, be stored thereby.

Thus, as FIG. 8 through FIG. 10, it may be that the water quality meter data processing device includes a configuration in which:

the tolerance value data includes tolerance value data pertaining to weights; and the measurement value data display unit 3*d* displays the measurement value data resulting from measurement by a weight gauge 15 of the body X1 being measured.

In accordance with such constitution, tolerance value data includes data pertaining to weight tolerance values, and measurement value data display unit 3*d* displays measurement value data resulting from measurement by weight gauge 15 of body X1 being measured. This makes it possible for weight values of body X1 being measured which are measured by a weight gauge and which are displayed by measurement value data display unit 3*d* to be compared with tolerance values which are displayed by reagent preparation data display unit 3*c*.

While there is no particular limitation with respect thereto, note that reagent preparation data arithmetic unit 43*a* may perform arithmetic operations with respect to dispensed amounts of raw materials based on measurement value data. For example, as shown in FIG. 10, after pure water has been dispensed, reagent preparation data arithmetic unit 43*a* might perform arithmetic operations with respect to the amount of Raw Material h (e.g., pH adjustment liquid) to be dispensed based on measurement value data acquired from water quality meter 11, and reagent preparation data display unit 3*c* might display the amount to be dispensed as determined by the arithmetic operations which have been performed.

Furthermore, while there is no particular limitation with respect thereto, before weight gauge 15 is used to carry out measurement of body X1 being measured, for example, it is sometimes the case, for example, that a standard (a weight or the like) is used to calibrate weight gauge 15. In such case, memory unit 42 might, for example, store data (e.g., calibration date and time or the like) pertaining to the calibration carried out at weight gauge 15; and moreover, data relating said calibration data and measurement value data acquired from weight gauge 15 might be stored thereby.

(2) Furthermore, the constitution of processing device 1 associated with FIG. 8 through FIG. 10 and the foregoing second embodiment is such that it comprises preparation process determination unit 43*b*. However, processing device 1 is not limited to such constitution. For example, it is also possible to adopt a constitution in which processing device 1 does not comprise preparation process determination unit 43*b*, confirmation of the preparation process being carried out by comparing measurement value data displayed by measurement value data display unit 3*d* and tolerance value data displayed by reagent preparation data display unit 3*c*.

(3) Furthermore, at processing device 1 associated with FIG. 8 through FIG. 10 and the foregoing second embodiment, preparation type data, preparation amount data, dispense order data, raw material type data, dispense amount data, and tolerance value data may be input at reagent preparation data input unit 2*d*, and related data memory unit 42*a* may store the data that has been input. This will make it possible for processing device 1 to add new reagent preparation data.

Third Embodiment

Next, a third embodiment at a water quality meter data processing device 1 will be described with reference to FIG. 11 and FIG. 12. At FIG. 11 and FIG. 12, note that portions assigned reference numerals identical to reference numerals at FIG. 1 through FIG. 10 indicate elements having constitutions more or less similar to, or functions (actions) more or less similar to, those described above, and that repetitive description thereof is omitted.

Water quality meter 11 associated with the present embodiment is a pH meter 11 which causes a measurement value resulting from measurement of body X1 being measured to be output in the form of an electrical signal (e.g., voltage value or electric current value). In addition, calibration solution(s) (e.g., calibration solution(s) of pH 4.0, 7.0, and/or 9.0) are used to carry out calibration of pH meter 11 so as to cause the pH value and the electrical signal to agree. For example, the value of the electrical signal when a calibration solution of pH 9.0 is measured might be established as the value of the electrical signal that indicates a pH of 9.0.

As shown in FIG. 11, input unit 2 comprises individual identification data input unit 2*a* at which data (individual identification data) for individual identification of water quality meter 11 is input. Furthermore, input unit 2 comprises calibration solution data input unit 2*e* at which data (calibration solution data) pertaining to the pH of a calibration solution serving as body X1 being measured is input, and calibration indication data input unit 2*f* at which data (calibration indication data) for indicating that pH meter 11 is to be calibrated is input.

Acquisition unit 41 comprises individual identification data acquisition unit 41*a* which acquires individual identification data, and calibration solution acquisition unit 41*e* which acquires calibration solution data. Furthermore, acquisition unit 41 comprises measurement value data acquisition unit 41*b* that acquires data (measurement value data) pertaining to the electrical signal output from pH meter 11, and measurement time data acquisition unit 41*c* that acquires data (measurement time data) pertaining to times of acquisition of data pertaining to the electrical signal from pH meter 11.

Stating this another way, measurement value data acquisition unit 41*b* acquires data (measurement value data) pertaining to the electrical signal resulting from measurement by pH meter 11 of the calibration solution which serves as body X1 being measured, and measurement time data acquisition unit 41*c* acquires data (measurement time data) pertaining to times of measurement by pH meter 11 of the calibration solution which serves as body X1 being measured. Moreover, when calibration indication data is input at calibration indication data input unit 2*f*, measurement value data acquisition unit 41*b* acquires measurement value data, and measurement time data acquisition unit 41*c* acquires measurement time data.

Memory unit 42 comprises related data memory unit 42*a* which stores related data. In accordance with the present embodiment, related data is data relating calibration solution data and measurement value data. That is, related data includes data (more specifically, calibration solution data) related to body X1 being measured.

Next, a data processing method for water quality meter data processing device 1 associated with a third embodiment will be described with reference to FIG. 11 and FIG. 12.

First, during calibration of pH meter 11, individual identification data is input at individual identification data input unit 2*a*, and individual identification data acquisition unit 41*a* acquires said individual identification data. Furthermore, calibration solution data pertaining to the calibration solution to be used is input at calibration solution data input unit 2*e*, and calibration solution data acquisition unit 41*e* acquires said calibration solution data.

Figure 12:
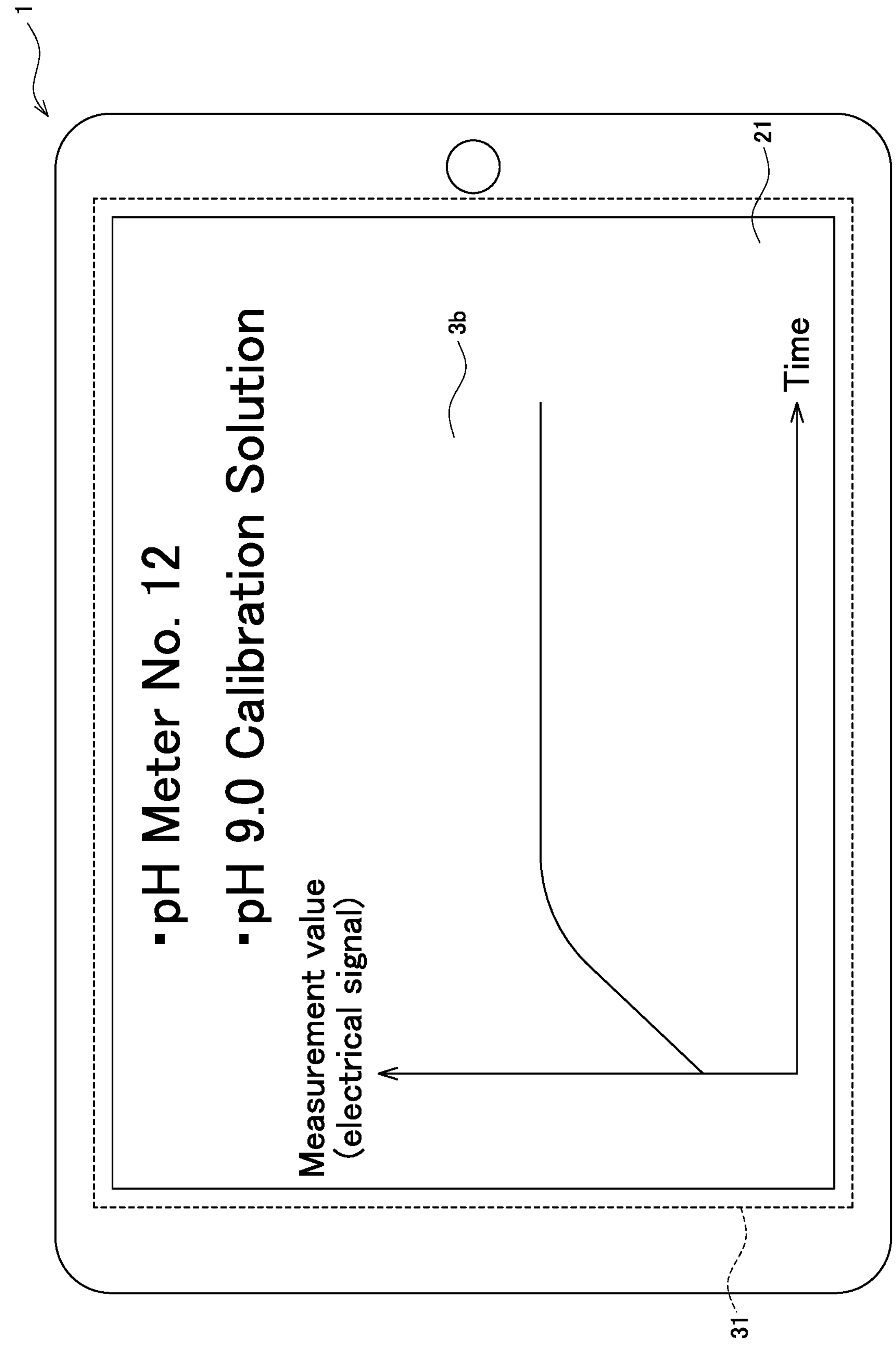
FIG. 12 is a drawing to assist in explaining data processing which may occur at a water quality meter data processing device associated with same embodiment.

For example, as shown in FIG. 12, display 31 might display individual identification data and calibration solution data. At FIG. 12, the individual identification data is "pH Meter No. 12", and the calibration solution data is "pH 9.0 Calibration Solution".

Furthermore, individual identification data and/or calibration solution data might, for example, be number(s) and/or the like; and might, for example, be input at respective input units 2*a*, 2*e* arranged at touch panel 21. Furthermore, individual identification data and/or calibration solution data might, for example, be bar code(s), QR code(s), and/or the like; and might, for example, be input respective input units 2*a*, 2*e* by way of image capture unit 1*a*.

Then, if calibration indication data is input at calibration indication data input unit 2*f*, this causes measurement value data acquisition unit 41*b* to acquire measurement value data, and causes measurement time data acquisition unit 41*c* to acquire measurement time data. In addition, related data, which is data relating calibration solution data and measurement value data, is stored at related data memory unit 42*a*.

In addition, display 31 might comprise related data display unit 3*b* as shown in FIG. 12; and in addition, related data display unit 3*b* might cause related data, which is data relating calibration solution data and measurement value data, to be displayed. This will make it possible to, at a future time, confirm the calibration status of pH meter 11.

For example, where the value of the electrical signal output by pH meter 11 differs greatly from the expected value of the electrical signal, a determination might be made that an abnormality exists with respect to the calibration solution (e.g., the wrong calibration solution was used, degradation of calibration solution caused deviation in pH to occur, etc.). It will thus be possible to carry out verification with respect to abnormalities at pH meter 11 and/or abnormalities at the calibration solution.

As described above, the water quality meter data processing device 1, according to this embodiment, that processes measurement value data which is data pertaining to measurement values resulting from measurement by a water quality meter 11 of a body X1 being measured, the water quality meter data processing device 1 comprises:

- a measurement value data acquisition unit 41*b* that acquires the measurement value data; and
- a memory unit 42 that stores related data which includes data related to at least one of either the body X1 being measured or the water quality meter 11 (the body X1 being measured in this embodiment).

In accordance with such constitution, measurement value data, which is data pertaining to measurement values resulting from measurement by water quality meter 11 of body X1 being measured, is acquired; and related data, which includes data related to at least one of either body X1 being measured or water quality meter 11, is stored. This will make it possible for processing of measurement value data to be carried out in accordance with data related to water quality meter 11 and/or body X1 being measured.

Further, as in this embodiment, it may be that the water quality meter data processing device 1 includes a configuration in which:

the water quality meter 11 is a pH meter 11 that causes the measurement value resulting from measurement of the body X1 being measured to be output as an electrical signal;

the water quality meter data processing device 1 further comprises a calibration solution data acquisition unit 41*e* that acquires calibration solution data which is data pertaining to a pH of a calibration solution which is the body X1 being measured;

the measurement value data acquisition unit 41*b* acquires the measurement value data which is data pertaining to the electrical signal that is output from the pH meter 11; and the related data is data relating the calibration solution data and the measurement value data.

In accordance with such constitution, calibration solution data, which is data pertaining to the pH of the calibration solution serving as body X1 being measured, is acquired; and measurement value data, which is data pertaining to the electrical signal output by pH meter 11, is acquired. In addition, because related data is data relating calibration solution data and measurement value data, this makes it possible to, at a future time, confirm the calibration status of pH meter 11.

Fourth Embodiment

Next, a fourth embodiment at a water quality meter data processing device 1 will be described with reference to FIG. 13 and FIG. 14. At FIG. 130 and FIG. 14, note that portions assigned reference numerals identical to reference numerals at FIG. 1 through FIG. 12 indicate elements having constitutions more or less similar to, or functions (actions) more or less similar to, those described above, and that repetitive description thereof is omitted.

Figure 14:
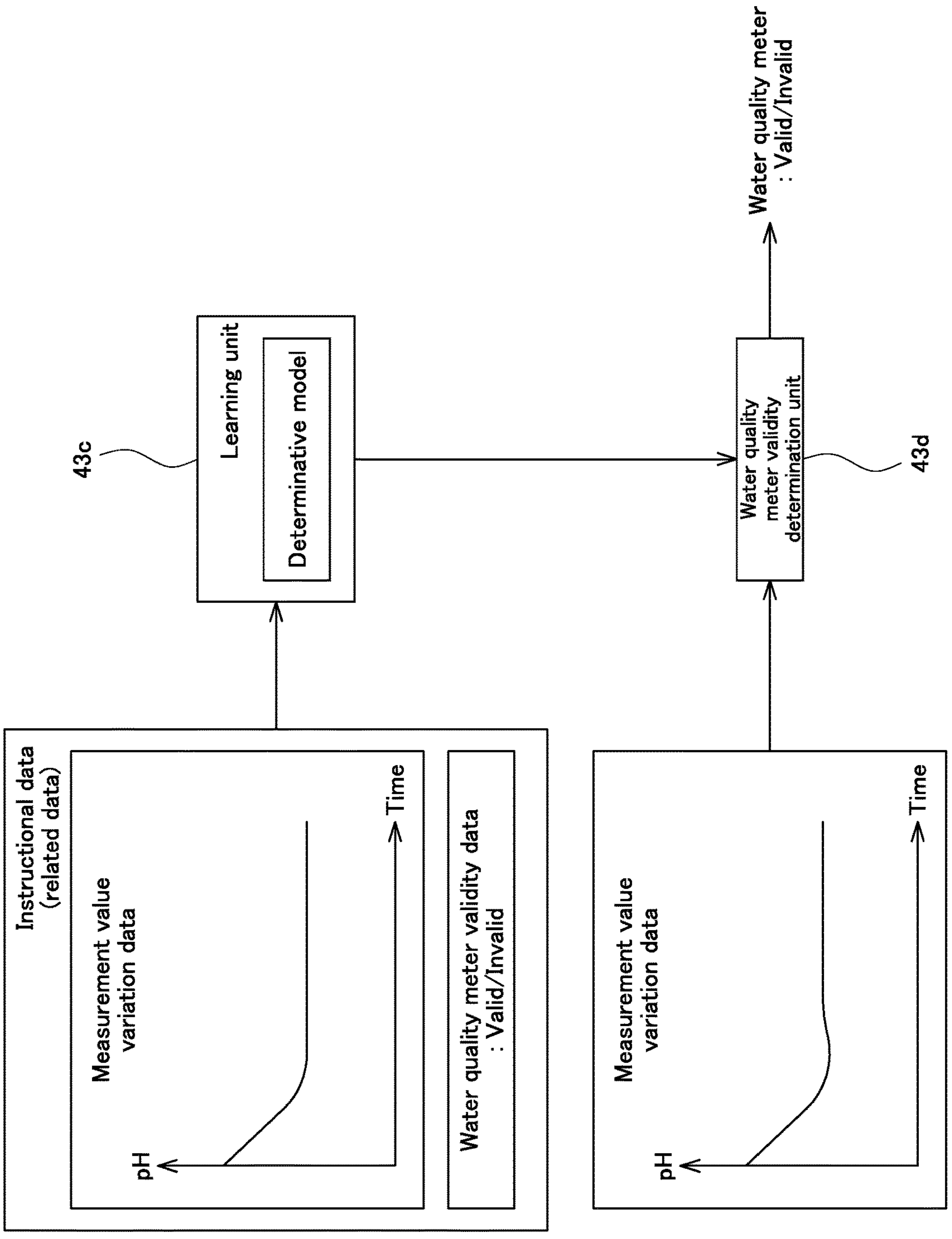
FIG. 14 is a drawing to assist in explaining data processing which may occur at a water quality meter data processing device associated with same embodiment.

As shown in FIG. 13 and FIG. 14, memory unit 42 comprises related data memory unit 42*a* which stores related data. In accordance with the present embodiment, related data is data relating water quality meter validity data which is data pertaining to the validity of water quality meter 11 and measurement value variation data which is data pertaining to variation in measurement value data as a function of passage of measurement time. That is, related data includes data (more specifically, water quality meter validity data) related to water quality meter 11.

Input unit 2 comprises related data input unit 2*g* at which input of related data is carried out, and measurement indication data input unit 2*b* at which data (measurement indication data) for indicating that body X1 being measured is to be measured by water quality meter 11 is input. Note that related data might, for example, be sent thereto from various water quality meters 11 by means of communication means 14. That is, data pertaining to various water quality meters 11 may be stored at and accumulated by related data memory unit 42*a*.

Acquisition unit 41 comprises related data acquisition unit 41*f* which acquires related data. Furthermore, acquisition unit 41 comprises measurement value data acquisition unit 41*b* that acquires data (measurement value data) pertaining to measurement values resulting from measurement by water quality meter(s) 11 of body X1 being measured, and measurement time data acquisition unit 41*c* that acquires data (measurement time data) pertaining to times of measurement by water quality meter(s) 11 of body X1 being measured.

Arithmetic unit 43 comprises learning unit 43*c* which engages in machine learning based on instructional data stored at related data memory unit 42*a*. More specifically, learning unit 43*c* uses related data, which relates measurement value variation data and water quality meter validity data, as instructional data to engage in machine learning of a determinative model in which measurement value variation data serves as input and water quality meter validity data serves as output. While there is no particular limitation with respect thereto, learning unit 43*c* might, for example, engage in learning of a neural network through utilization of deep learning.

Furthermore, arithmetic unit 43 comprises water quality meter validity determination unit 43*d* which uses a determinative model resulting from machine learning by learning unit 43*c* to determine the validity of water quality meter(s) 11 from particular measurement value variation data. While there is no particular limitation with respect thereto, water quality meter validity determination unit 43*d* may, for example, utilize a neural network, learning of which has been completed, to output water quality meter validity data from particular measurement value variation data.

In addition, water quality meter validity data that has been output by water quality meter validity determination unit 43*d* might, for example, be displayed by display 31 of output unit 3. Because this will make it possible for the validity of water quality meter(s) 11 to be determined based on related data (instructional data) from various water quality meters 11, this will make it possible to appropriately determine the validity of water quality meter(s) 11.

In addition, data resulting from determination might, for example, be stored at memory unit 42 in such fashion as to be related to individual identification data pertaining to said water quality meter(s) 11. For example, individual identification data for said water quality meter 11 (e.g., the water quality meter 11 itself or an electrode or component part of water quality meter 11) might, for example, be a number or the like, and might be input at touch panel 21; and/or might, for example, be a bar code, QR code, and/or the like, and might be input at input unit 2 by way of image capture unit 1*a* (and/or might be acquired by acquisition unit 41).

Note that instructional data used by learning unit 43*c* might, for example, include at least one among data (manufacturing lot data) pertaining to the manufacturing lot of water quality meter 11, data (cumulative time used data) pertaining to the cumulative time that water quality meter 11 has been used, data (sensitivity data) pertaining to the sensitivity of water quality meter 11, data (improper potential data) pertaining to the asymmetry potential of water quality meter 11, data (image capture data) resulting from image capture of water quality meter 11, and the like. In addition, water quality meter validity determination unit 43*d* may use not only measurement value variation data but also additionally at least one set of data among manufacturing lot data, cumulative time used data, sensitivity data, improper potential data, image capture data, and the like to determine the validity of water quality meter 11.

Furthermore, instructional data used by learning unit 43*c* might be data resulting from extraction of characteristic portion(s) from measurement value variation data. For example, instructional data might be that data which among measurement value variation data results from extraction of the time period before stabilization of measurement value data, or results from extraction of the time period after stabilization of measurement value data. In addition, water quality meter validity determination unit 43*d* may determine the validity of water quality meter 11 from data that has been extracted from among measurement value variation data.

As described above, the water quality meter data processing device 1, according to this embodiment, that processes measurement value data which is data pertaining to measurement values resulting from measurement by a water quality meter 11 of a body X1 being measured, the water quality meter data processing device 1 comprises:

a measurement value data acquisition unit 41*b* that acquires the measurement value data; and a memory unit 42 that stores related data which includes data related to at least one of either the body X1 being measured or the water quality meter 11 (the water quality meter 11 in this embodiment).

In accordance with such constitution, measurement value data, which is data pertaining to measurement values resulting from measurement by water quality meter 11 of body X1 being measured, would be acquired; and related data, which includes data related to at least one of either body X1 being measured or water quality meter 11, would be stored. This will make it possible for processing of measurement value data to be carried out in accordance with data related to water quality meter 11 and/or body X1 being measured.

Further, as in this embodiment, it may be that the water quality meter data processing device 1 includes a configuration in which:

the related data is data relating water quality meter validity data which is data pertaining to validity of the water quality meter 11 and measurement value variation data which is data pertaining to variation in the measurement value data as a function of passage of measurement time; and the water quality meter data processing device 1 further comprises:

a learning unit 43*c* that uses the related data as instructional data to engage in machine learning of a determinative model in which the measurement value variation data serves as input and the water quality meter validity data serves as output; and a water quality meter validity determination unit 43*d* that uses the determinative model to determine the validity of the water quality meter 11 from a particular one of the measurement value variation data.

In accordance with such constitution, learning unit 43*c* would use related data, which relates measurement value variation data and water quality meter validity data, as instructional data to engage in machine learning of a determinative model in which measurement value variation data serves as input and water quality meter validity data serves as output. In addition, water quality meter validity determination unit 43*d* would use a determinative model to determine the validity of water quality meter(s) 11 from particular measurement value variation data. This will make it possible to appropriately determine the validity of water quality meter 11.

The processing system 10, processing device 1 and processing method is not limited to the configuration of the embodiment described above, and the effects are not limited to those described above. It goes without saying that the processing system 10, processing device 1 and processing method can be variously modified without departing from the scope of the subject matter of the present invention. For example, the constituents, methods, and the like of the plurality of embodiments described above can be arbitrarily employed and combined (the constituents, methods, and the like of one embodiment can be applied to the constituents, methods, and the like of the other embodiments), and the constituents, methods, and the like of various modified examples described below may be arbitrarily selected and employed as the constituents, methods, and the like of the embodiments described above, as a matter of course.

List of Reference Characters

1 water quality meter data processing device
1*a* image capture unit
1*b* communication unit
2 input unit
2*a* individual identification data input unit
2*b* measurement indication data input unit
2*c* image capture indication data input unit
2*d* reagent preparation data input unit
2*e* calibration solution data input unit
2*f* calibration indication data input unit
2*g* related data input unit
2*h* weight gauge measurement indication data input unit
2*i* water quality meter measurement indication data input unit
3 output unit
3*a* temporal variation data display unit
3*b* related data display unit
3*c* reagent preparation data display unit
3*d* measurement value data display unit
3*e* determination data display unit
4 processing unit
4*a* processor
4*b* memory
4*c* interface
4*d* program
10 water quality meter data processing system
11 water quality meter
12 memory device
13 control device
14 communication mean
15 weight gauge
21 touch panel
22 button
23 microphone
31 display
32 speaker
41 acquisition unit
41*a* individual identification data acquisition unit
41*b* measurement value data acquisition unit
41*c* measurement time data acquisition unit
41*d* image capture data acquisition unit
41*e* calibration solution acquisition unit
41*f* related data acquisition unit
42 memory unit
42*a* related data memory unit
43 arithmetic unit
43*a* reagent preparation data arithmetic unit
43*b* preparation process determination unit
43*c* learning unit
43*d* water quality meter validity determination unit
44 control unit
X1 body being measured

The invention claimed is:

1. A water quality meter data processing device comprising:

a processor that processes measurement value data which is data pertaining to measurement values resulting from measurement by a water quality meter of a body being measured;

a measurement value data memory that acquires the measurement value data; and a related data memory that stores related data which includes data related to at least one of either the body being measured or the water quality meter, wherein the related data is reagent preparation data for preparation of a reagent by causing a plurality of raw materials to be dispensed, the related data includes raw material type data which is data pertaining to types of the raw materials. dispense order data which is data pertaining to an order in which the raw materials are dispensed, dispense amount data which is data pertaining to amounts of the raw materials dispensed, and tolerance value data which is data pertaining to tolerance values for the measurement value data when the raw materials are dispensed, and the water quality meter data processing device further comprises a reagent preparation data display unit that displays the reagent preparation data, and a measurement value data display unit that displays the measurement value data.

2. The water quality meter data processing device according to claim 1 further comprising:

an individual identification data memory that acquires individual identification data which is data for individual identification of the body being measured; and a measurement time data memory that acquires measurement time data which is data pertaining to times of measurement by the water quality meter of the body being measured;

wherein the related data is data relating to the individual identification data, the measurement value data, and the measurement time data.

3. The water quality meter data processing device according to claim 2 further comprising:

an image capture data memory that acquires image capture data which is data resulting from image capture of the body being measured;

wherein the related data is data relating to the measurement time data and the measurement value data when the body being measured underwent image capture, the image capture data, and the individual identification data.

4. The water quality meter data processing device according to claim 1 wherein:

the water quality meter is a pH meter that measures a pH of the body being measured;

the tolerance value data includes tolerance value data for the pH; and the measurement value data display unit displays the measurement value data of the body being measured by the pH meter.

5. The water quality meter data processing device according to claim 4 wherein:

the tolerance value data further includes tolerance value data pertaining to weights; and the measurement value data display unit further displays the measurement value data resulting from measurement by a weight gauge of the body being measured.

6. The water quality meter data processing device according to claim 1 wherein:

the water quality meter is a pH meter that causes the measurement value resulting from measurement of the body being measured to be output as an electrical signal;

the water quality meter data processing device further comprises a calibration solution data memory that acquires calibration solution data which is data pertaining to a pH of a calibration solution which is the body being measured;

the measurement value data memory acquires the measurement value data which is data pertaining to the electrical signal that is output from the pH meter; and the related data is data relating to the calibration solution data and the measurement value data.

7. The water quality meter data processing device according to claim 1 wherein the related data is data relating to water quality meter validity data which is data pertaining to validity of the water quality meter and measurement value variation data which is data pertaining to variation in the measurement value data as a function of passage of measurement time; and the processor further comprises:

a learning processor that uses the related data as instructional data to engage in machine learning of a determinative model in which the measurement value variation data serves as input and the water quality meter validity data serves as output; and a water quality meter validity determination processor that uses the determinative model to determine the validity of the water quality meter from a particular one of the measurement value variation data.

8. A water quality meter data processing system comprising:

at least one water quality meter; and the water quality meter data processing device according to claim 1.

9. A water quality meter data processing method comprising:

executing, by a processor of a computer, processing measurement value data which is data pertaining to measurement values resulting from measurement by a water quality meter of a body being measured;

acquiring, by a measurement value data memory, the measurement value data; and storing, by a related data memory, related data which includes data related to at least one of either the body being measured or the water quality meter, wherein the related data is reagent preparation data for preparation of a reagent by causing a plurality of raw materials to be dispensed, the related data includes raw material type data which is data pertaining to types of the raw materials, dispense order data which is data pertaining to an order in which the raw materials are dispensed, dispense amount data which is data pertaining to amounts of the raw materials dispensed, and tolerance value data which is data pertaining to tolerance values for the measurement value data when the raw materials are dispensed; and the water quality meter data processing method further comprises displaying, through a reagent preparation data display unit, the reagent preparation data, and displaying, through a measurement value data display unit, the measurement value data.

* * * * *